(12) United States Patent
Paulowski et al.

(10) Patent No.: US 12,193,662 B2
(45) Date of Patent: Jan. 14, 2025

(54) FIRING CIRCUIT AND CONTROL ALGORITHM FOR SURGICAL STAPLER

(71) Applicant: Cilag GmbH International, Zug (CH)

(72) Inventors: Joseph D. Paulowski, Butler, KY (US); Shane R. Adams, Lebanon, OH (US); Nicholas J. Ross, Franklin, OH (US); Johnnie Bell, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 1001 days.

(21) Appl. No.: 16/930,613

(22) Filed: Jul. 16, 2020

(65) Prior Publication Data

US 2022/0015761 A1  Jan. 20, 2022

(51) Int. Cl.
*A61B 17/072* (2006.01)
*A61B 17/00* (2006.01)
*A61B 17/29* (2006.01)

(52) U.S. Cl.
CPC .. *A61B 17/072* (2013.01); *A61B 2017/00017* (2013.01); *A61B 2017/00398* (2013.01); *A61B 2017/00734* (2013.01); *A61B 2017/07228* (2013.01); *A61B 2017/07257* (2013.01); *A61B 2017/07271* (2013.01); *A61B 2017/07278* (2013.01); *A61B 2017/07285* (2013.01); *A61B 2017/2925* (2013.01)

(58) Field of Classification Search
CPC .................. A61B 17/072; A61B 2017/07285
See application file for complete search history.

(56) References Cited

U.S. PATENT DOCUMENTS

| | | | |
|---|---|---|---|
| 7,404,508 B2 | 7/2008 | Smith et al. | |
| 7,434,715 B2 | 10/2008 | Shelton, IV et al. | |
| 7,644,848 B2 | 1/2010 | Swayze et al. | |
| 7,721,930 B2 | 5/2010 | McKenna et al. | |

(Continued)

FOREIGN PATENT DOCUMENTS

| | | |
|---|---|---|
| EP | 1813203 A2 | 8/2007 |
| EP | 3231372 A2 | 10/2017 |

OTHER PUBLICATIONS

International Search Report and Written Opinion dated Oct. 13, 2021, for International Application No. PCT/IB2021/056392, 15 pages.

*Primary Examiner* — Gloria R Weeks
(74) *Attorney, Agent, or Firm* — Frost Brown Todd LLP

(57) ABSTRACT

A surgical instrument includes a body having a firing actuator, a shaft, a motor, an end effector, and a control circuit. The motor is configured to activate in response to a firing actuation of the firing actuator. The end effector is operable to staple and sever tissue and includes a cutting edge configured to selectively translate longitudinally between a proximal position and a distal position in response to an activation of the motor. The control circuit is configured to generate a forward motor control signal to pulsate the cutting edge. The forward motor control signal includes a first time duration including movement of the cutting edge distally from the proximal position to a second longitudinal position, a second time duration including ceased movement of the cutting edge, and a third time duration including movement of the cutting edge distally from the second longitudinal position toward the distal position.

20 Claims, 17 Drawing Sheets

(56) References Cited

U.S. PATENT DOCUMENTS

| | | | |
|---|---|---|---|
| 8,028,885 B2* | 10/2011 | Smith | A61B 90/03 |
| | | | 227/176.1 |
| 8,210,411 B2 | 7/2012 | Yates et al. | |
| 8,408,439 B2 | 4/2013 | Huang et al. | |
| 8,453,914 B2 | 6/2013 | Laurent et al. | |
| 8,523,043 B2* | 9/2013 | Ullrich | A61B 17/072 |
| | | | 227/19 |
| 9,186,142 B2 | 11/2015 | Fanelli et al. | |
| 9,517,065 B2 | 12/2016 | Simms et al. | |
| 9,622,746 B2 | 4/2017 | Simms et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 10,092,292 B2 | 10/2018 | Boudreaux et al. | |
| 10,238,386 B2* | 3/2019 | Overmyer | A61B 17/068 |
| 2007/0270790 A1* | 11/2007 | Smith | A61B 17/1114 |
| | | | 606/1 |
| 2008/0056865 A1* | 3/2008 | Laing | B65B 69/0033 |
| | | | 414/412 |
| 2010/0276471 A1* | 11/2010 | Whitman | A61B 17/1114 |
| | | | 227/180.1 |
| 2013/0168431 A1* | 7/2013 | Zemlok | A61B 17/068 |
| | | | 227/175.1 |
| 2013/0206814 A1* | 8/2013 | Morgan | A61B 17/105 |
| | | | 606/1 |
| 2014/0305994 A1* | 10/2014 | Parihar | A61B 17/07207 |
| | | | 227/180.1 |
| 2015/0272572 A1* | 10/2015 | Overmyer | A61B 90/98 |
| | | | 227/177.1 |
| 2015/0272575 A1* | 10/2015 | Leimbach | A61B 90/96 |
| | | | 227/175.3 |
| 2016/0066916 A1* | 3/2016 | Overmyer | H02H 3/207 |
| | | | 227/176.1 |
| 2018/0360445 A1 | 12/2018 | Shelton, IV et al. | |
| 2018/0360455 A1 | 12/2018 | Shelton, IV et al. | |

* cited by examiner

FIRING CIRCUIT AND CONTROL ALGORITHM FOR SURGICAL STAPLER

Examples of surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents is incorporated by reference herein in its entirety.

BACKGROUND

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
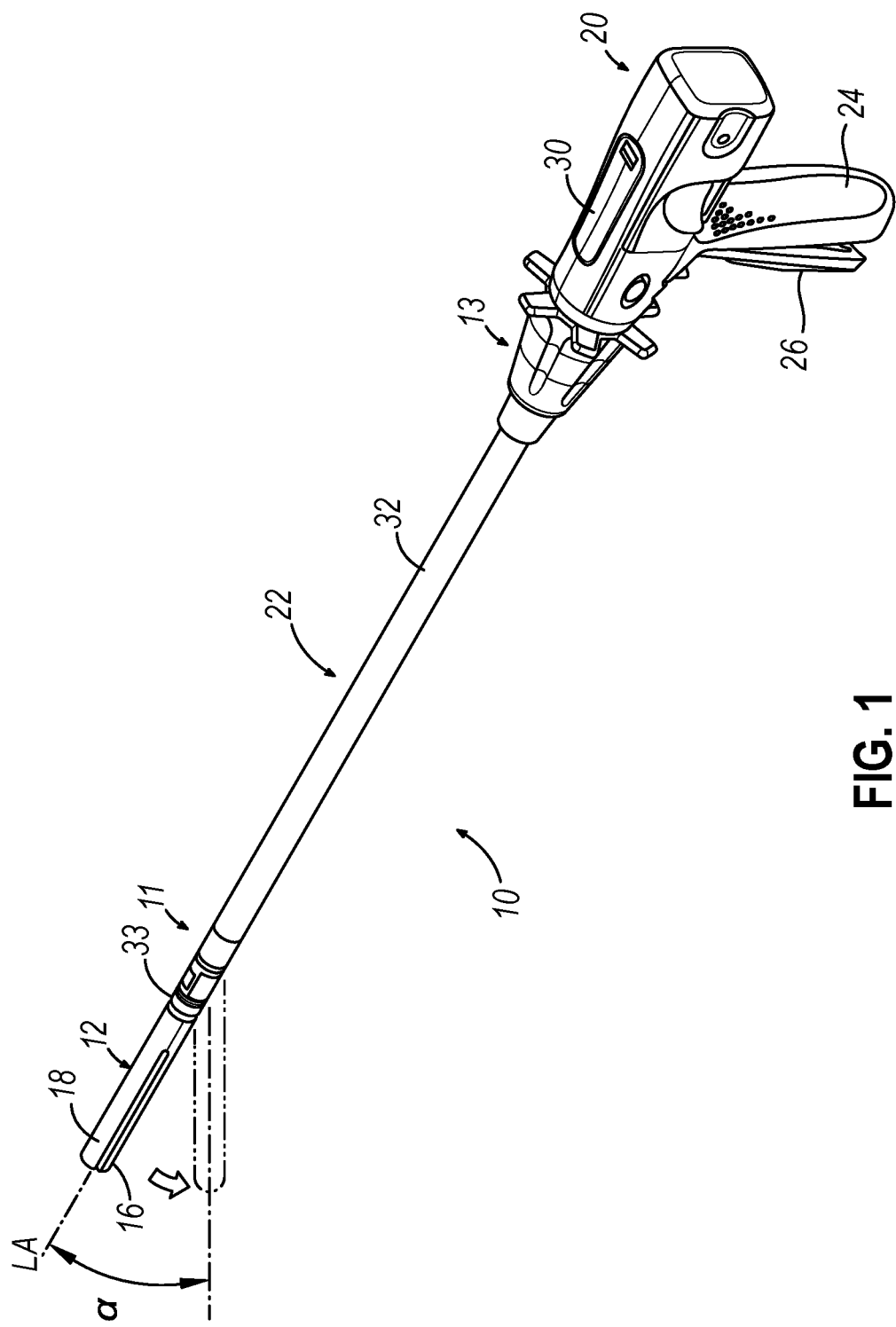
FIG. 1 depicts a perspective view of an exemplary articulating surgical stapling instrument.
Figure 2:
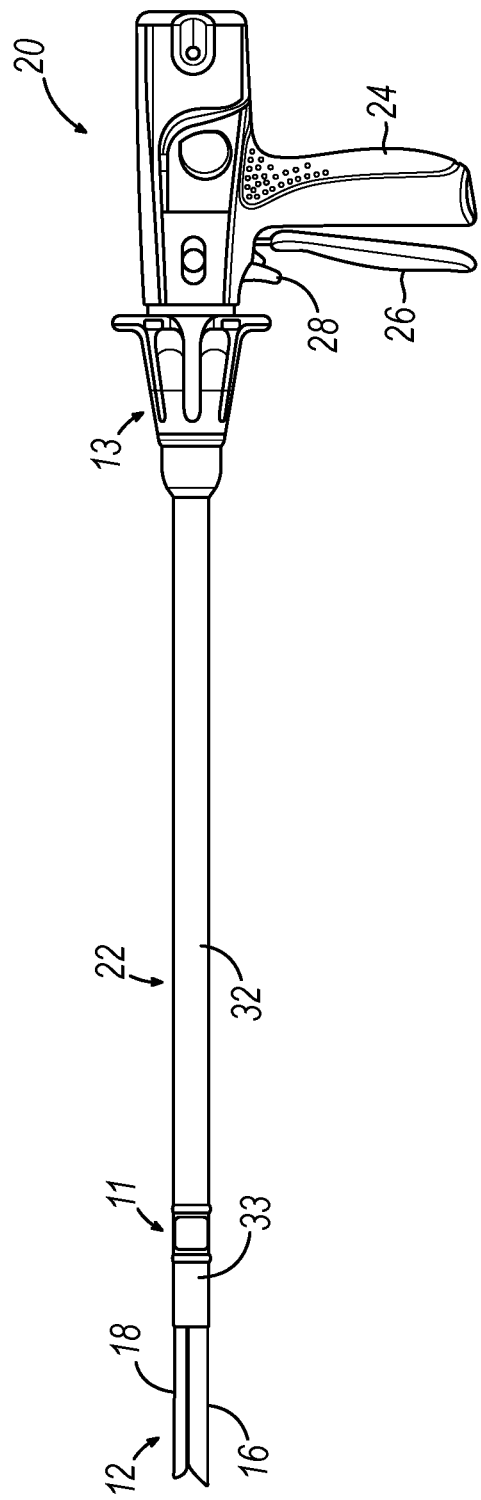
FIG. 2 depicts a side view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-7 depict an example of a surgical stapling and severing instrument (10) that is sized for insertion, in a nonarticulated state as depicted in FIG. 1, through a trocar cannula, thoracotomy, or other incision to a surgical site in a patient for performing a surgical procedure. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20).

Once articulation joint (11) and end effector (12) are inserted into the patient, articulation joint (11) may be remotely articulated, as depicted in phantom in FIG. 1, by an articulation control (13), such that end effector (12) may be deflected from the longitudinal axis (LA) of shaft (22) at a desired angle (a). By way of example only, articulation joint (11) and/or articulation control (13) may be constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein in its entirety; and/or U.S. Pat. No. 9,795,379, entitled "Surgical Instrument with Multi-Diameter Shaft," issued Oct. 24, 2017, the disclosure of which is incorporated by reference herein in its entirety.

Other suitable forms that articulation joint (11) and articulation control (13) may take will be apparent to those skilled in the art in view of the teachings herein.

End effector (12) of the present example includes a lower jaw (16) and an upper jaw in the form of a pivotable anvil (18). By way of example only, lower jaw (16) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein in its entirety. Anvil (18) may be constructed and operable in accordance with at least some of the teachings of at least some of the teachings of U.S. Pat. No. 10,092,292, entitled "Staple Forming Features for Surgical Stapling Instrument," issued Oct. 9, 2018, the disclosure of which is incorporated by reference herein in its entirety. Other suitable forms that lower jaw (16) and anvil (18) may take will be apparent to those skilled in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to transmit longitudinal movement from closure tube (32) to closure ring (33).

Handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of tissue clamped in end effector (12), as will be described in greater detail below. Thereafter, triggers (26, 28) may be released to release the tissue from end effector (12).

Figure 4A:
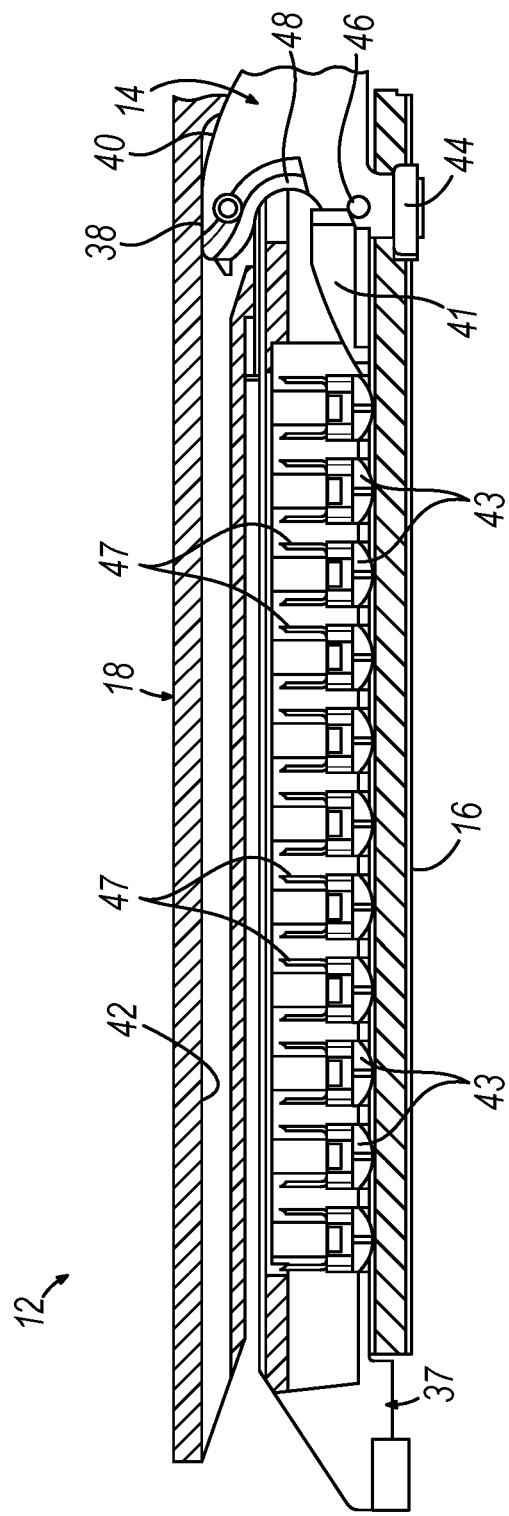
FIG. 4A depicts a side cross-sectional view of the end effector of FIG. 3, taken along line 4-4 of FIG. 3, with the firing beam in a proximal position.
Figure 4B:
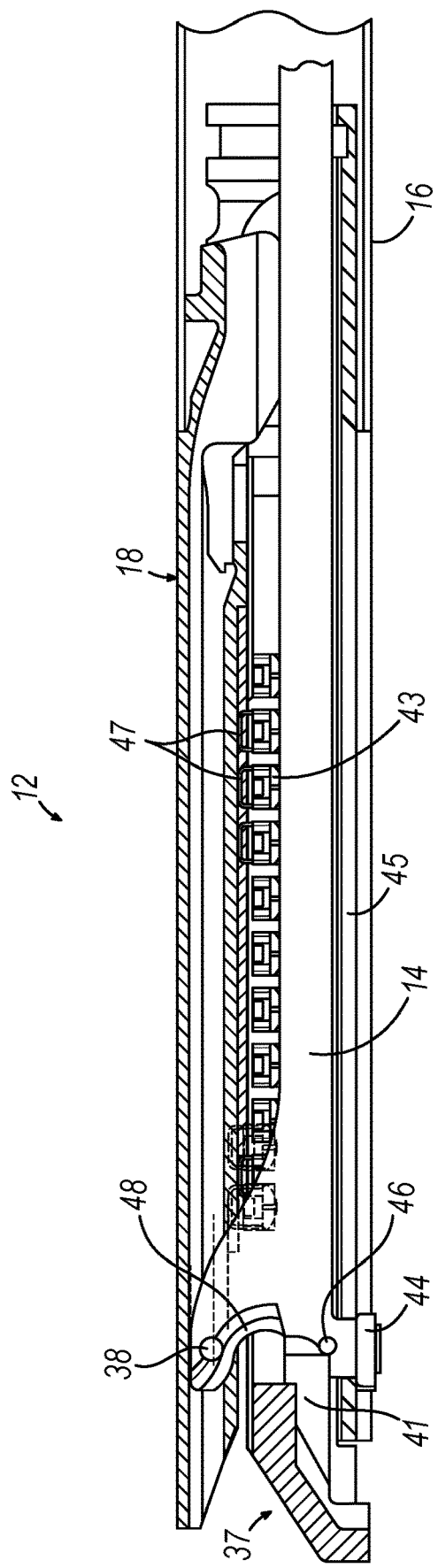
FIG. 4B depicts a side cross-sectional view of the end effector of FIG. 3, taken along line 4-4 of FIG. 3, with the firing beam in a distal position.

As best seen in FIGS. 4A-4B, firing beam (14) of the present example includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing. By way of example only, firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein in its entirety. Other suitable forms that firing beam (14) may take will be apparent to those skilled in the art in view of the teachings herein.

Figure 3:
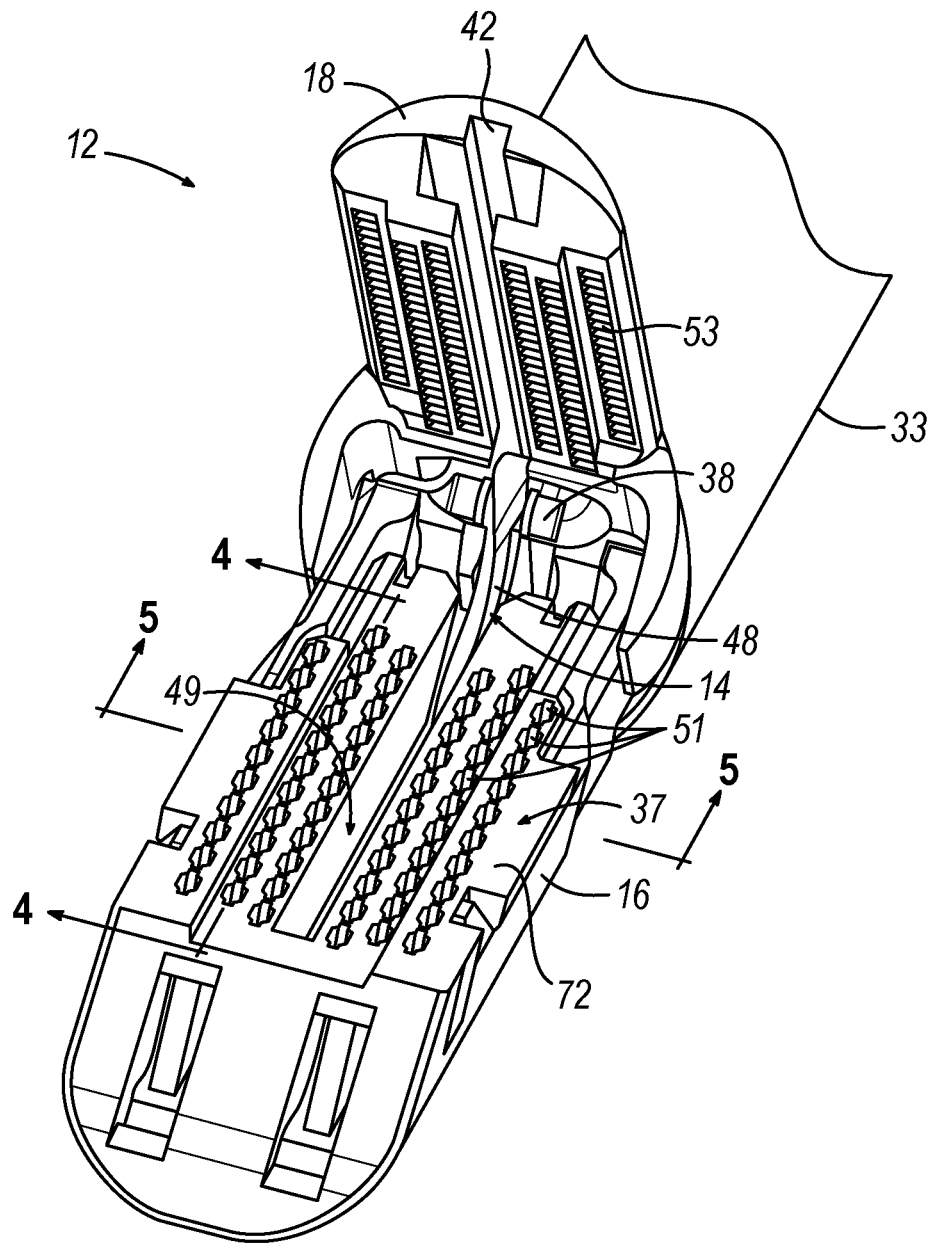
FIG. 3 depicts a perspective view of an opened end effector of the instrument of FIG. 1.
Figure 5:
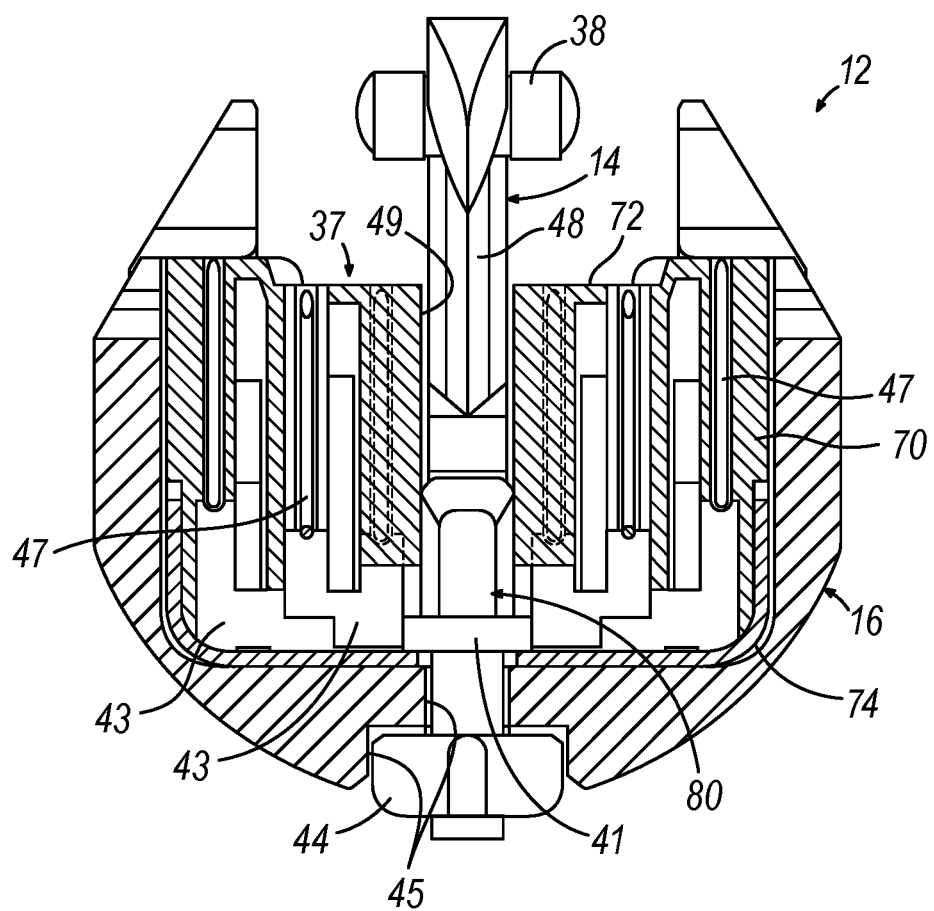
FIG. 5 depicts an end cross-sectional view of the end effector of FIG. 3, taken along line 5-5 of FIG. 3.
Figure 6:
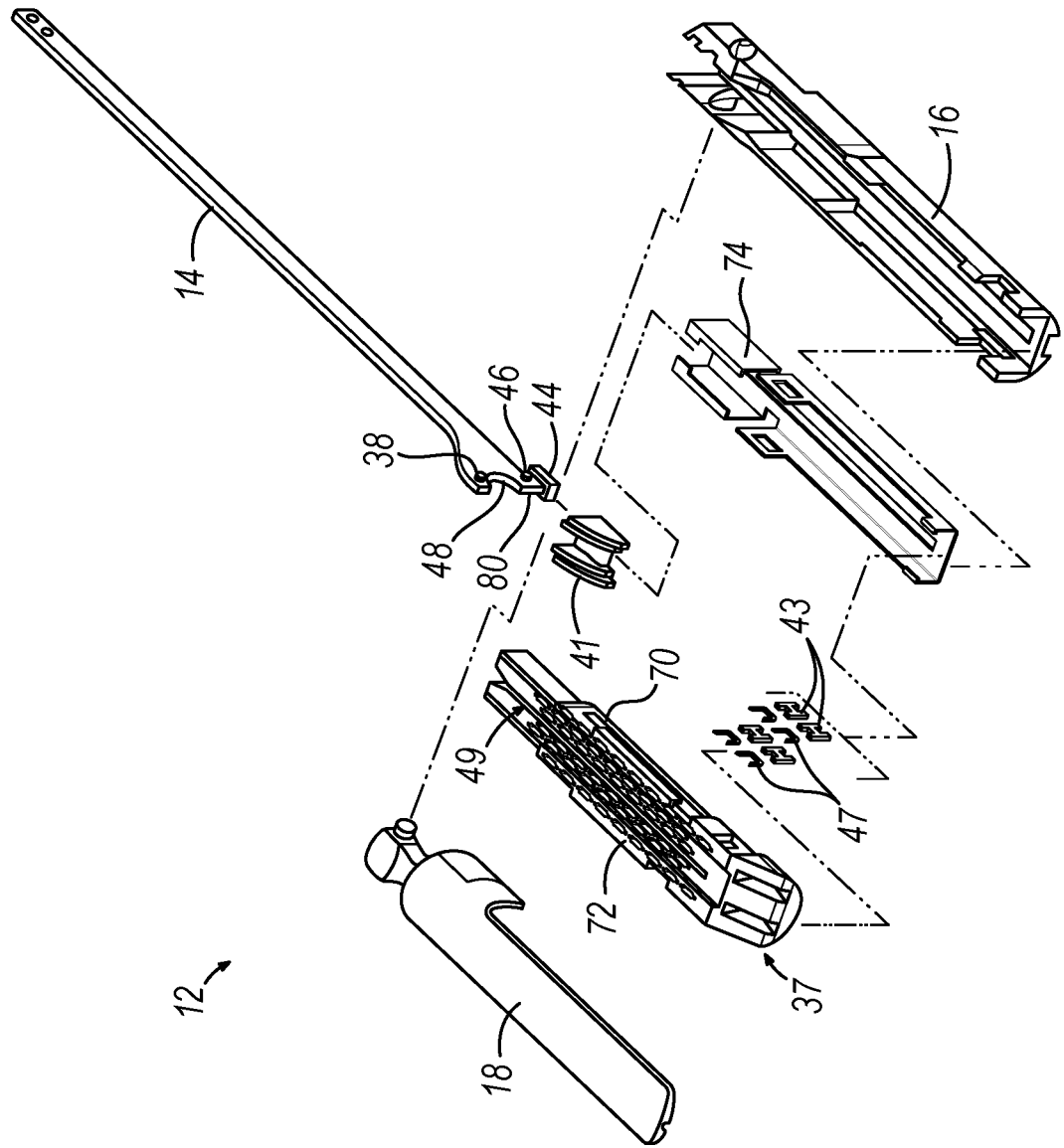
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

By way of example only, staple cartridge (37) may be constructed and operable in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein in its entirety. Other suitable forms that staple cartridge (37) may take will be apparent to those skilled in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14), and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
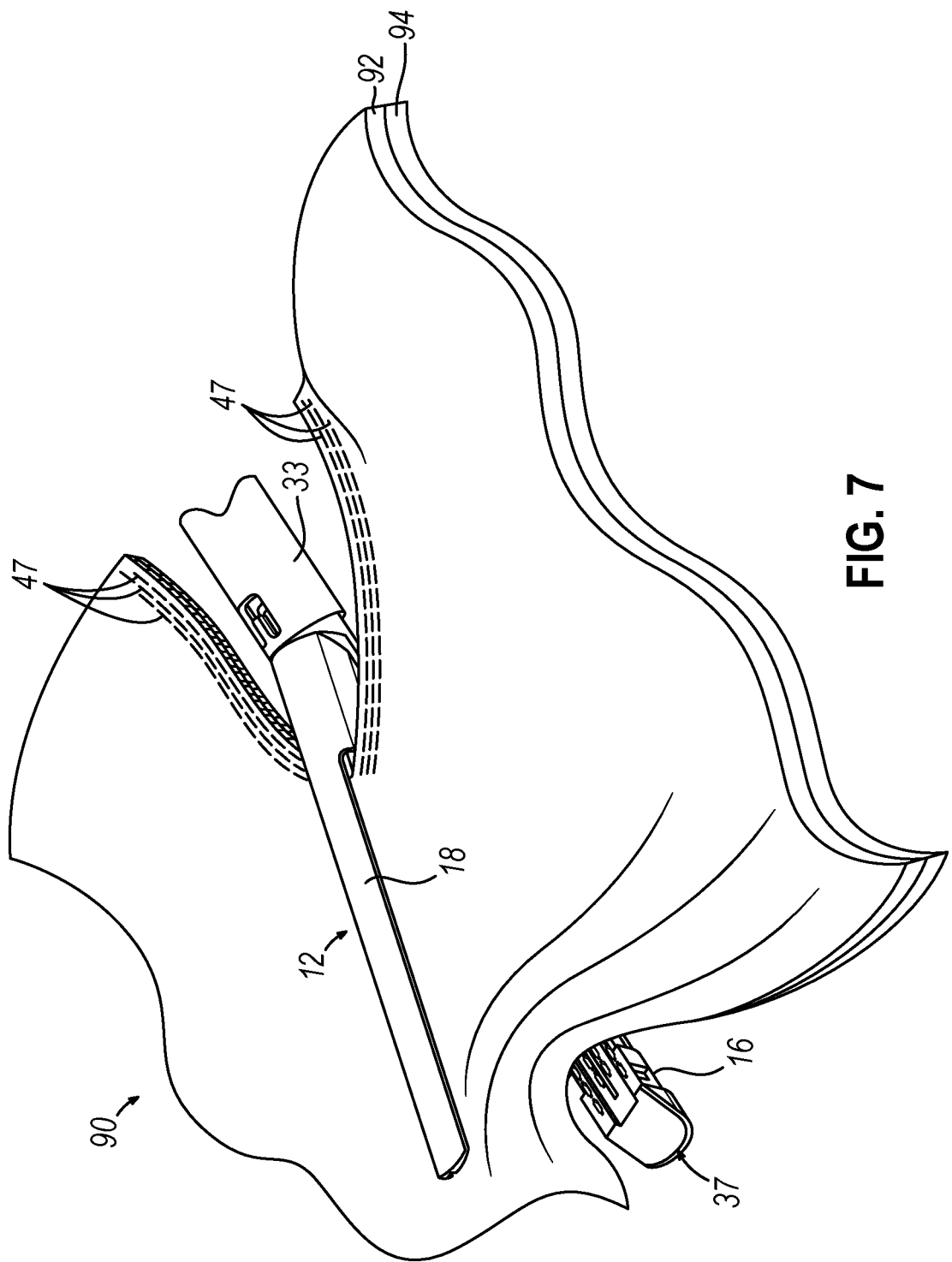
FIG. 7 depicts a perspective view of the end effector of FIG. 3, positioned at tissue and having been actuated once in the tissue.

FIG. 7 shows end effector (12) having been actuated through a single stroke through tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47)

may be positioned at any suitable orientations. In the present example, end effector (12) is withdrawn from the trocar after the first stroke is complete, spent staple cartridge (37) is replaced with a new staple cartridge, and end effector (12) is then again inserted through the trocar or incision to reach the stapling site for further cutting and stapling. This process may be repeated until the desired number of cuts and staples (47) have been provided. Anvil (18) may need to be closed to facilitate insertion and withdrawal through the trocar; and anvil (18) may need to be opened to facilitate replacement of staple cartridge (37).

In some versions, instrument (10) provides motorized control of firing beam (14). By way of example only, such motorization may be provided in accordance with at least some of the teachings of U.S. Pat. No. 9,622,746, entitled "Distal Tip Features for End Effector of Surgical Instrument," issued Apr. 18, 2017, the disclosure of which is incorporated by reference herein in its entirety; and/or U.S. Pat. No. 8,210,411, entitled "Motor-Driven Surgical Instrument," issued Jul. 3, 2012, the disclosure of which is incorporated by reference herein in its entirety. Other suitable components, features, and configurations for providing motorization of firing beam (14) will be apparent to those skilled in the art in view of the teachings herein. It should also be understood that some other versions may provide manual driving of firing beam (14), such that a motor may be omitted.

In motorized versions of instrument (10), instrument (10) may also include a manual return switch, or "bail out switch," (104) (see, FIG. 8) positioned on or within handle portion (20), such as within or under a user-accessible panel or "bail out door" (30), the bail out switch (104) being configured to enable the operator to quickly begin retracting firing beam (14) proximally during a firing stroke. In other words, bail out switch (104) may be manually actuated when firing beam (14) has only been partially advanced distally. Bail out switch (104) may provide further functionality in accordance with at least some of the teachings of U.S. Pat. No. 9,622,746, entitled "Distal Tip Features for End Effector of Surgical Instrument," issued Apr. 18, 2017, the disclosure of which is incorporated by reference herein. To access the bail out switch (104), the operator first opens the bailout door (30).

II. Exemplary Firing Circuits and Control Algorithms

A. Overview

As previously described with reference to FIGS. 1-7, various components are operable to translate firing beam (14) for stapling and severing clamped tissue via end effector (12). In some versions, a motor is configured to activate to actuate end effector (12) in response to a firing actuation of firing trigger (28), first in a "forward" direction advance firing beam (14) distally to cut and staple tissue, and next in a "backward" direction to retract firing beam (14) proximally once the cutting and stapling has been completed. Once the two-stage firing stroke is complete (i.e., a stapling operation has concluded and cutting edge (48) and firing beam (14) have been retracted), the motor is configured to deactivate. Further, the motor can be controlled using a firing circuit and/or control algorithm to actuate end effector (12) at one or more predetermined speeds through the firing stroke, thereby providing a predetermined time period for completing the firing stroke. In some examples, the predetermined time period may range from approximately 1 second in duration to approximately 10 seconds in duration. In other examples, the predetermined time period may range from approximately 3 seconds in duration to approximately 7 seconds in duration.

Figure 8:
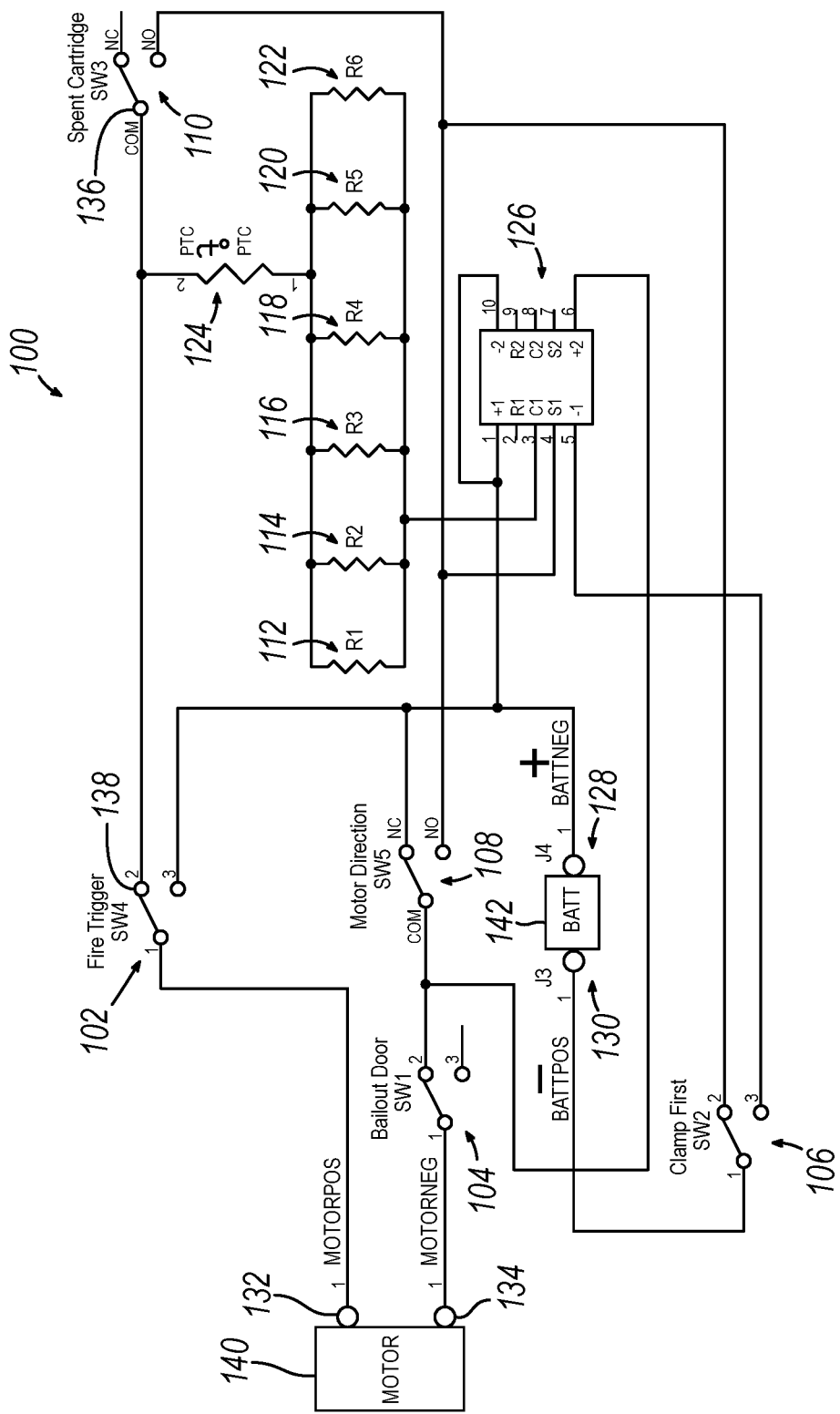
FIG. 8 depicts a schematic view of an exemplary control circuit that may be incorporated into the instrument of FIG. 1.

In the present example, instrument (10) provides motorized control of firing beam (14). FIG. 8 is an exemplary control circuit (100) that may be incorporated into instrument (10) to provide motorized control of firing beam (14). In particular, FIG. 8 shows an exemplary control circuit (100) that may be used to power an electric motor (140) with electric power from a battery (142). The motor (140) is operable to translate firing beam (14) longitudinally in a manner as will be described in greater detail below. It should be understood that the entire control circuit (100), including motor (140) and battery (142), may be housed within handle portion (20). By way of example only, motor (140) may be incorporated into instrument (10) in accordance with at least some of the teachings of U.S. Pat. No. 8,453,914, the disclosure of which is incorporated by reference herein in its entirety.

As shown, control circuit (100) of this example includes several switches (102, 104, 106, 108, 110), several resistors (112, 114, 116, 118, 120, 122), a thermistor (124), and a relay (126), these components of which being configured and operable to selectively couple the positive and negative terminals (128, 130) of battery (142) with the positive and negative terminals (132, 134) of motor (140) to selectively power motor (140).

More specifically, control circuit (100) of the present example includes a fire trigger switch (102), which is configured to be actuated from the "3" position to the "2" position by an actuation firing trigger (28). Control circuit (100) also includes a bail out switch (104), which is configured to be actuated from the "2" position to the "3" position to effectively disconnect the negative motor terminal upon actuation of bail out switch (104). Control circuit (100) also includes a clamp switch (106), which is configured to be actuated from the "3" position to the "2" position upon a determination that anvil (18) has sufficiently closed to permit a safe and effective firing stroke. Control circuit (100) also includes a motor direction switch (108). Once firing beam (14) reaches a distal-most position (e.g., at the end of a cutting stroke) and cartridge (37) is spent, switches (108, 136) automatically switch from first positions to second positions and relay (126) is latched "open," thereby reversing the polarity of the voltage applied to motor terminals (132, 134). This reverses the direction of rotation of motor (140), it being understood that the operator will have released closure trigger (26) at this stage of operation. Once actuation firing trigger (28) is released and fire trigger switch (102) is actuated back to the "3" position, relay (126) is latched "closed." In some versions, current flows through a reverse direction indicator (e.g., including an optional LED, etc.) to provide a visual indication to the operator that motor (140) rotation has been reversed. Various suitable ways in which switch (108) may be automatically switched to a second position when firing beam (14) reaches a distal-most position will be apparent to those skilled in the art in view of the teachings herein.

Still further, control circuit (100) includes spent cartridge switch (110), which is configured to be closed by default but is automatically opened in response to a lockout condition. By way of example only, a lockout condition may include one or more of the following: the absence of a cartridge (37) in lower jaw (16), the presence of a spent (e.g., previously fired) cartridge (37) in lower jaw (16), a determination that instrument (10) has been fired too many times, and/or any other suitable conditions. Various sensors, algorithms, and other features that may be used to detect lockout conditions will be apparent to those skilled in the art in view of the teachings herein. Similarly, other suitable kinds of lockout conditions will be apparent to those skilled in the art in view of the teachings herein. It should be understood that control circuit (100) is opened and thus motor (140) is inoperable when switch (110) is opened. A lockout indicator (110) (e.g., an LED, etc.) is operable to provide a visual indication of the status of lockout switch (108). By way of example only, lockout switch (108) and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein. While FIG. 8 shows various switches (102, 104, 106, 108, 110) in certain positions, it should be understood that each switch (102, 104, 106, 108, 110) is independently operable to perform a specific function and is therefore variable depending on the circumstances of operation of instrument (10) in a particular instance.

Resistors (112, 114, 116, 118, 120, 122) are operable to slow the initial stages of a firing stoke to allow time for spent cartridge switch (110) to operate, if necessary. Each resistor (112, 114, 116, 118, 120, 122) may be provided of equal value, for example, 47 ohms, or otherwise may be varied, or even omitted, as necessary.

In some versions, one or more of switches (102, 104, 106, 108, 110) are in the form of microswitches. Other suitable forms will be apparent to those skilled in the art in view of the teachings herein. In addition to or in lieu of the foregoing, at least part of control circuit (100) may be configured in accordance with at least some of the teachings of U.S. Pat. No. 8,210,411, entitled "Motor-Driven Surgical Instrument," issued Jul. 3, 2012, the disclosure of which is incorporated by reference herein.

In some instances, it may be desirable to modify instrument (10) to incorporate a pulsating "forward" firing stroke technique operable to more slowly advance the cutting edge (48) of firing beam (14) into tissue. By pulsing the cutting edge (48) into tissue, that is, longitudinally translating cutting edge (48) through a series of distal advancements separated by short pauses, the tissue is allowed time to relax as the stapling and cutting operation is performed, which may result in a more precise and effective operation. As described in greater detail below, various exemplary firing circuits can be included within instrument (10) to manipulate the power provided to motor (140) to successively activate and deactivate motor (140) during the "forward" cutting and stapling phase of the firing stroke thereby advancing the cutting edge (48) into the tissue in a pulsating manner. Thereafter, the control circuit may be operable to disable or otherwise bypass the pulsing portion of the firing circuit during the "backward" phase of the firing stroke to allow motor (140) to activate to retract firing beam (14) proximally through lower jaw (16) in one continuous motion (i.e., without pulsing).

In this example, and as will be described in greater detail below, motor (140) can be controlled using a firing circuit and/or control algorithm to actuate end effector (12) at one or more predetermined speeds through the firing stroke having a pulsating forward phase, thereby providing a longer predetermined time period for completing the firing stroke than in non-pulsating examples. In some examples utilizing a pulsating forward phase of the firing stroke, the predetermined time period to complete a full firing stroke (including both advancement and retraction of cutting edge (48)) may range from approximately 2 seconds in duration to approximately 18 seconds in duration. In other examples, the predetermined time period may range from approximately 6 seconds in duration to approximately 14 seconds in duration. Specifically, the predetermined time period for only the forward phase of the firing stroke (including the advancement of cutting edge (48)) may range from approximately 2 seconds in duration to approximately 10 seconds in duration. In other examples, the time period for only the forward phase of the firing stroke may range from approximately 3 seconds in duration to approximately 7 seconds in duration. Various factors may affect the time period required to complete the forward phase, such as friction, battery level, and cartridge (37) size. Additionally, motor (140) may require more activation cycles, thus a greater predetermined time period, for cutting and stapling procedures involving thick tissue than motor (140) does for thin tissue. In one merely illustrative example, motor (140) may pulse (i.e., transition from an OFF or deactivated state to an ON or activated state) 3-4 times over the course of 3 seconds for cutting and stapling thin tissue, while motor (140) may pulse 7-9 times over the course of 7 seconds for cutting and stapling thick tissue.

It should be understood that the various additions and alternatives to control circuit (100) described above may be readily used with instrument (10). It should also be understood that, in some instances, the configuration and arrangement of the electrical components of control circuit (100) may need to be varied in order to complement the configuration and arrangement of the alternative firing circuits described below. Various suitable ways in which the alternatives to control circuit (100) described below may be incorporated into instrument (10) will be apparent to those skilled in the art in view of the teachings herein.

B. Exemplary Pulsating Firing Circuit Using an RC Circuit and Transistors

Figure 9:
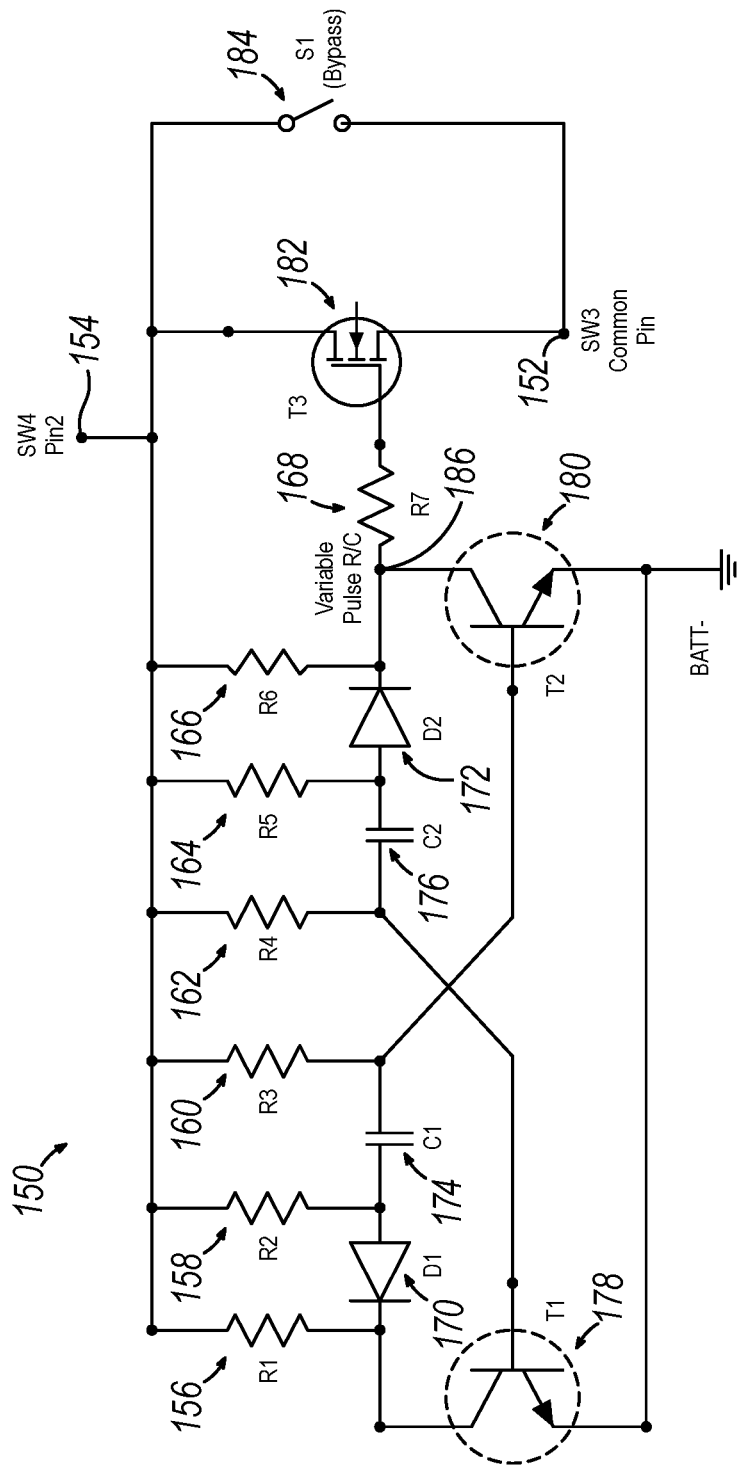
FIG. 9 depicts a first exemplary firing circuit that may be incorporated into the control circuit of FIG. 8.

Various pulsating firing circuits may be configured to manipulate the power provided to motor (140) to successively and repetitively activate and deactivate motor (140) during the "forward" cutting and stapling phase of the firing stroke thereby advancing the cutting edge (48) of firing beam (14) into the tissue in a pulsating manner. FIG. 9 depicts one exemplary pulsating firing circuit (150) which can be coupled with control circuit (100), or otherwise integrated into control circuit (100). Particularly, node (152) of circuit (150) may be coupled with node (136) of control circuit (100), and node (154) of circuit (150) may be coupled with node (138) of control circuit (100) to include cutting edge (48) pulsing techniques to instrument (10). As shown, firing circuit (150) of this example includes several resistors (156, 158, 160, 162, 164, 166, 168), diodes (170, 172), capacitors (174, 176), transistors (178, 180, 182), and switch (184).

In the present example, transistors (178, 180) may each be an NPN bipolar junction transistor, for example, a 2N3904 General Purpose Transistor manufactured by ON Semiconductor, Inc. Alternatively, any other suitable kinds of transistors may be used. Diodes (170, 172) can be, for example, 1N4148 Small Signal Diodes manufactured by ON Semiconductor, Inc. Alternatively, any other suitable kinds of diodes may be used. Further, resistors (156, 158, 160, 162, 164, 166, 168) of the present example can be chosen at 470 ohms, 390 ohms, 12.5 kiloohms, 12.5 kiloohms, 390 ohms, 470 ohms, and 470 ohms, respectively. Alternatively, any other resistance values may be used. Capacitors (174, 176)

can be chosen at 115 microfarads and 58 microfarads, respectively. Alternatively, any other capacitance values may be used.

Firing circuit (150) is thereby configured and operable as an astable multi-vibrator circuit to output a square wave voltage signal, consisting of alternating HIGH and LOW voltage outputs, to node (186) which are formed by alternate switching of transistors (178. 180), where the peak amplitude of the HIGH voltage output signal is approximately equal to the amplitude of input signal at node (154). Transistor (182) can be a MOSFET transistor, for example, an SIS476DN-T1-GE3 N-Channel 30 V (D-S) MOSFET manufactured by Vishay Intertechnology, Inc. Alternatively, any other suitable kind of transistor may be used. Transistor (182) can be provided to selectively allow electrical current to pass between nodes (152, 154) as the astable multi-vibrator output square waveform remains in the HIGH state at node (186), and disallow electrical current to pass between nodes (152, 154) as the astable multi-vibrator output square waveform remains in the LOW state at node (186).

Figure 10:
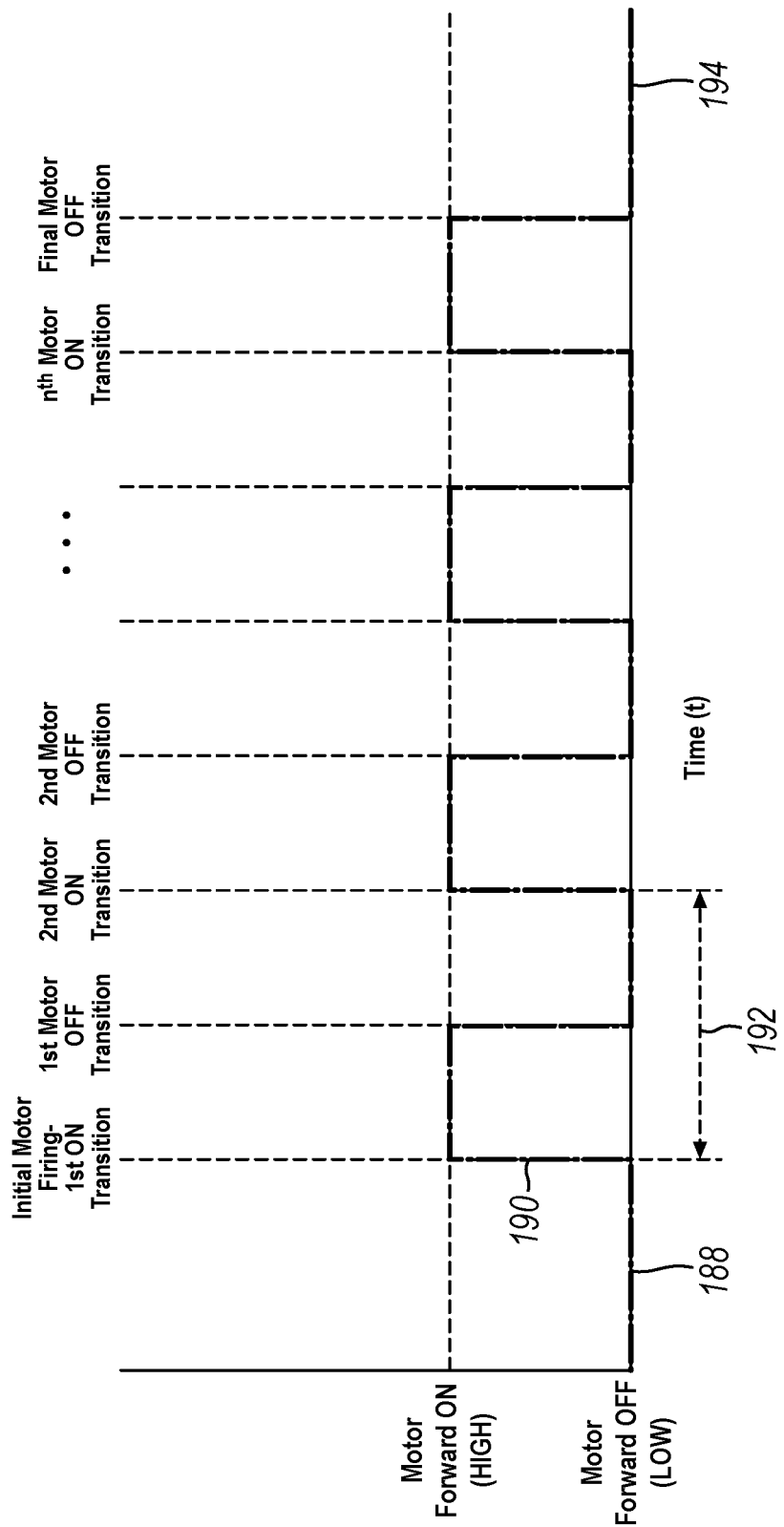
FIG. 10 depicts a graph illustrating the relationship between a firing motor position and an output of the firing circuit of FIG. 9, with the firing circuit configured for pulsed-firing mode and actuated for a cutting and stapling operation.

FIG. 10 depicts an example voltage output waveform received at node (186) of FIG. 9. As described above, firing circuit (150) is powered upon receiving a power signal from positive battery terminal (130) initiated in part by an actuation of fire trigger switch (102). Unless and until firing circuit (150) receives a power signal, the output waveform at node (186) will remain at a LOW state as shown in initial phase (188). Upon receiving a power signal at node (154), the astable multi-vibrator circuitry (i.e., resistors (156, 158, 160, 162, 164, 166), capacitors (174, 176), diodes (170. 172), and transistors (178. 180)) is enabled and operable to repeatedly output a square wave signal (190) until fire trigger switch (102) is released and electrical current ceases flowing into node (152).

In some examples, it may be desirable to pulse the cutting edge (48) forward in two pulses, therefore any number of square wave periods ranging from approximately 1.5 periods to approximately 2.0 periods. In other examples it may be desirable to pulse the cutting edge (48) forward in three or more pulses, therefore requiring approximately 2.5 or more square wave periods. It may be further desirable to modify the length of a time period (192) of signal (190). In the present example, the frequency of signal (190) ranges from approximately 0.5 hertz to approximately 3.0 hertz. In alternative examples, the frequency of signal (190) may range from approximately 0.75 hertz to approximately 2.0 hertz. In other alternative examples, the frequency of signal (190) may be at or approximately 1.5 hertz (i.e., 1.5 seconds in length, 1.0 seconds HIGH and 0.5 seconds LOW). In other examples, resistor (156, 158, 160, 162, 164, 166) and capacitor (174, 176) values may be altered to adjust time period (192) as required. While the duty cycle of signal (190) is approximately 50%, in various other examples the duty cycle of signal (190) may be selected to be 0%, 25%, 75%, 100%, or some other value. However, it should be understood that various alternative duty cycles may be configured.

In the present example, firing circuit (150) is not utilized to provide power to motor (140) to retract the cutting edge (48) from the tissue. Rather, once the cutting operating is complete, motor direction switch (108) of control circuit (100) toggles from the first state to the second state, causing the power signal to be removed from node (154), such that the output provided at node (152) of firing circuit (150) returns to a LOW state (194).

Still further, it may be desirable to include a bypass mechanism to permit an operator of instrument (10) to bypass the pulse-inducing features of firing circuit (150), such as in an instance where the operator wishes to cut a vessel or for any other reason dictated by the circumstances, and instead advance the cutting edge (48) in one continuous motion (i.e., via signal (190) having a duty cycle of 100%) as shown in FIG. 8. In this example, a user-actuatable bypass switch (184), for example an ON/OFF rocker switch or other switch form commonly used in the art that is easily actual by a user, may be included on an exterior surface of instrument (10), such as on handle portion (20) of instrument (10).

C. Exemplary Pulsating Firing Circuit Using an RC Circuit and Timer

Figure 11:
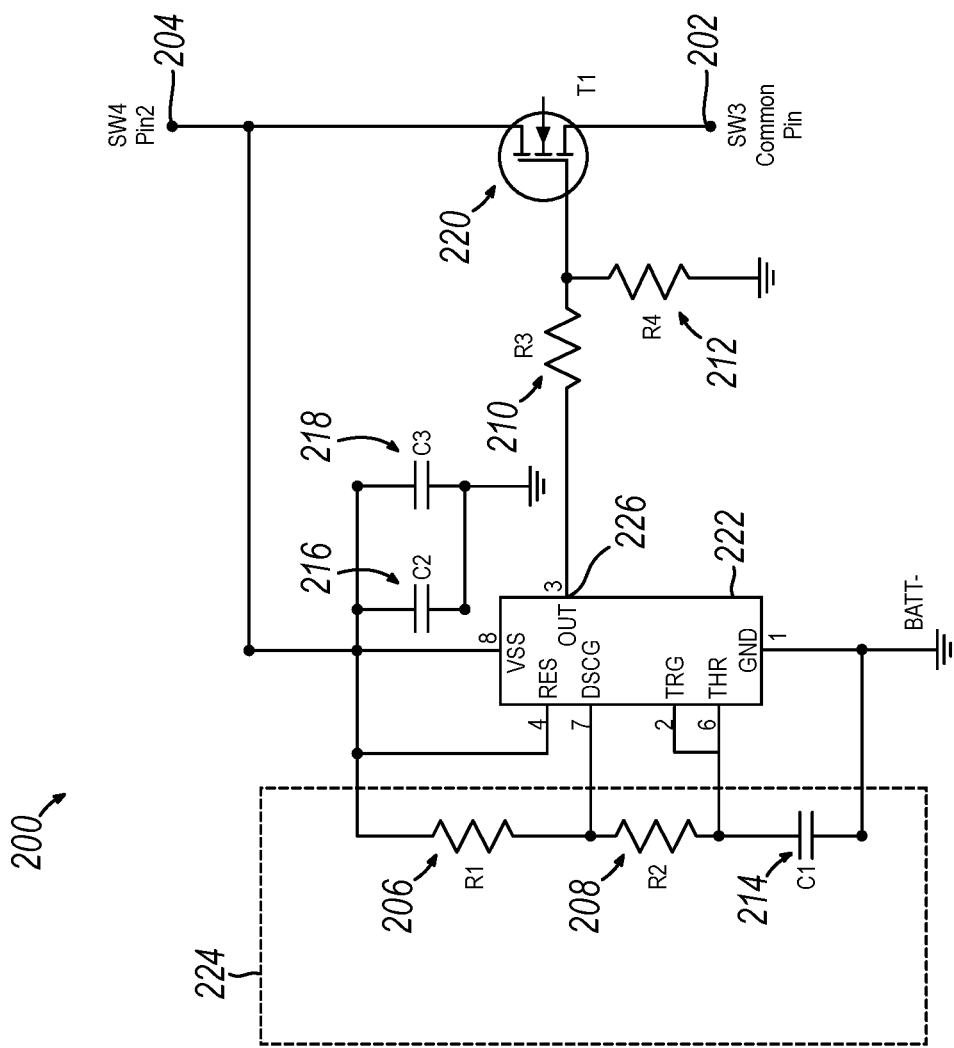
FIG. 11 depicts a second exemplary firing circuit that may be incorporated into the control circuit of FIG. 8.
Figure 12:
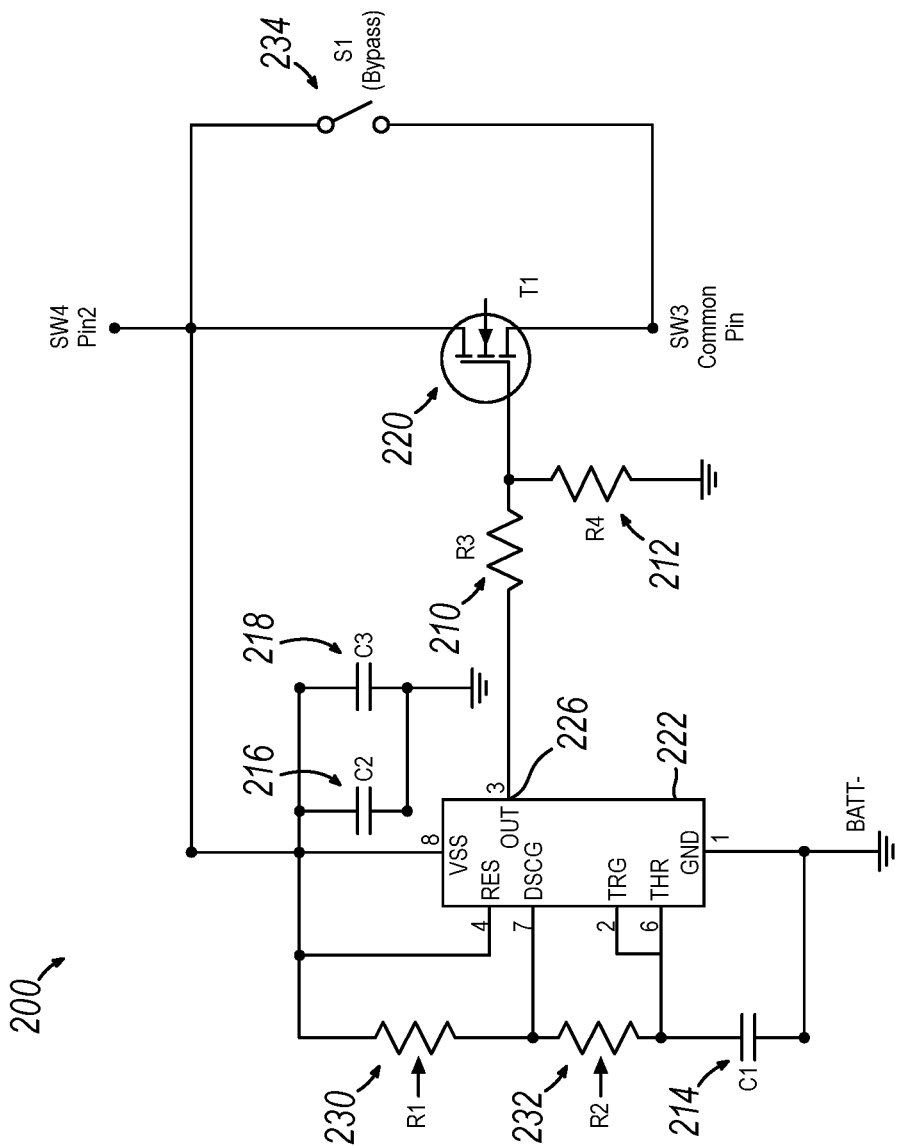
FIG. 12 depicts the firing circuit of FIG. 11, and including a pulse-adjustment mechanism and a pulse-bypass mechanism.

FIGS. 11-12 depict another exemplary firing circuit (200) that may be incorporated into instrument (10). Particularly, node (202) of circuit (200) may be coupled with node (136) of control circuit (100), and node (204) of circuit (200) may be coupled with node (138) of control circuit (100) to include cutting edge (48) pulsing techniques to instrument (10). As shown, firing circuit (200) of this example includes several resistors (206, 208, 210, 212), capacitors (214, 216, 218), a transistor (220), and a timer (222). Transistor (220) can be a MOSFET transistor, for example, an SIS476DN-T1-GE3 N-Channel 30 V (D-S) MOSFET manufactured by Vishay Intertechnology, Inc. Alternatively, any other suitable kind of transistor may be used. Further, timer (222) can be, for example, a LMC555 CMOS Low-Power Timer manufactured by Texas Instruments, Inc. It will be appreciated that in other examples timer (222) may take various other suitable forms apparent to those skilled in the art in view of the teachings herein.

Timer (222) of the present example is a single integrated chip functioning similar to a multi-vibrator. Timer (222) is operable in three different modes: astable mode, bistable mode, and monostable mode. In astable mode, as will be described below, timer (222) outputs an oscillating pulse signal or waveform. Particularly, output (226) of timer (222) oscillates between a HIGH state and a LOW state at a configurable frequency and pulse width. At the conclusion of the adjustable duration, timer (222) returns to a steady LOW state output unless and until the external trigger activates timer (222) again. Thus, output (226) is configurable to resemble the waveform illustrated in FIG. 10.

Particularly, RC circuit (224), comprising resistors (206, 208) and capacitor (214), is configurable by changing the resistor (206, 208) and capacitor (214) values to adjust the oscillating square waveform provided at an output (226) of the timer (222). With reference to FIG. 10, the duration of one full period (192) can be calculated using the following approximate equation: T=0.693(R1+2R2)*C, where T is equal to the length of time of one period (192), R1 is resistor (206), R2 is resistor (208) and C is capacitor (214). In the present example, resistors (206, 208, 210, 212) can be chosen at 22 kiloohms, 16 kiloohms, 470 ohms, and 10 kiloohms, respectively. Alternatively, any other suitable resistance values may be used. Capacitors (214, 216, 218) can be chosen at 47 microfarads, 0.01 microfarads, and 1 microfarad, respectively. Alternatively, any other suitable kinds of capacitor values may be used.

As firing circuit (200) is configured and operable to output a square wave voltage signal consisting of alternating HIGH and LOW voltage outputs at output node (226), transistor (182) can further be provided to selectively allow electrical current to pass between nodes (202, 204) as the output square waveform remains in the HIGH state at node (226), and disallow electrical current to pass between nodes (202, 204) as the astable multi-vibrator output square waveform remains in the LOW state at node (226).

In some examples, it may be desirable to pulse the cutting edge (48) of firing beam (14) forward in two pulses, therefore requiring 1.5-2 square wave periods. In other examples it may be desirable to pulse the cutting edge (48) forward in three or more pulses, therefore requiring 2.5 or more square wave periods. It may be further desirable to modify the length of one period (192) of signal (190). In the present example, a single period (192) may be one second in length (i.e., 0.5 seconds HIGH, 0.5 seconds LOW). In other examples, values of RC circuit (224) may be altered to adjust period (192) as required. In various examples, the duty cycle of signal (190) may be selected to be 0%, 25%, 50%, 75%, 100%; however, it should be understood that various alternative duty cycles may be configured.

In the present example, firing circuit (200) is not utilized to provide power to motor (140) to retract the cutting edge (48) from the tissue. Rather, once the cutting operating is complete, motor direction switch (108) of control circuit (100) toggles from the first state to the second state, causing the power signal to be removed from node (204), such that the output provided at node (226) of firing circuit (200) returns to a LOW state (194).

It may be desirable to provide a version of firing circuit (200) that includes features that allow a user of instrument (10) to adjust the pulsing motion (i.e., adjust the period (192)), or to selectively bypass the pulsing features altogether. FIG. 12 shows an example of firing circuit (200) that provides a user with the real-time ability to adjust the values of resistors (206, 208) described above. Particularly, resistors (206, 208) may be substituted with potentiometers (230, 232). Potentiometers (230, 232) may be actuatable via one or more user-adjustable dials which may be included on instrument (10), such as on handle portion (20) of instrument (10). In one example, potentiometer (230) may be adjustable from 1-30 kiloohms and potentiometer (232) may be adjustable from 1-25 kiloohms. However, it should be understood that the values of potentiometers (230, 232) may be varied in order to meet the requirements of alternative configurations of instrument (10).

Also as depicted in FIG. 12, circuit (200) of the present example can include a bypass mechanism to permit an operator of instrument (10) to bypass the pulse-inducing features of firing circuit (200) and instead advance cutting edge (48) of firing beam (14) in one continuous motion (i.e., via signal (190) having a duty cycle of 100%), such as shown in FIG. 8. In this example, a user-actuatable bypass switch (234), for example an ON/OFF rocker switch or other switch form commonly used in the art that is easily actuated by a user, may be included on an exterior surface of instrument (10), such as on handle portion (20) of instrument (10).

Figure 13:
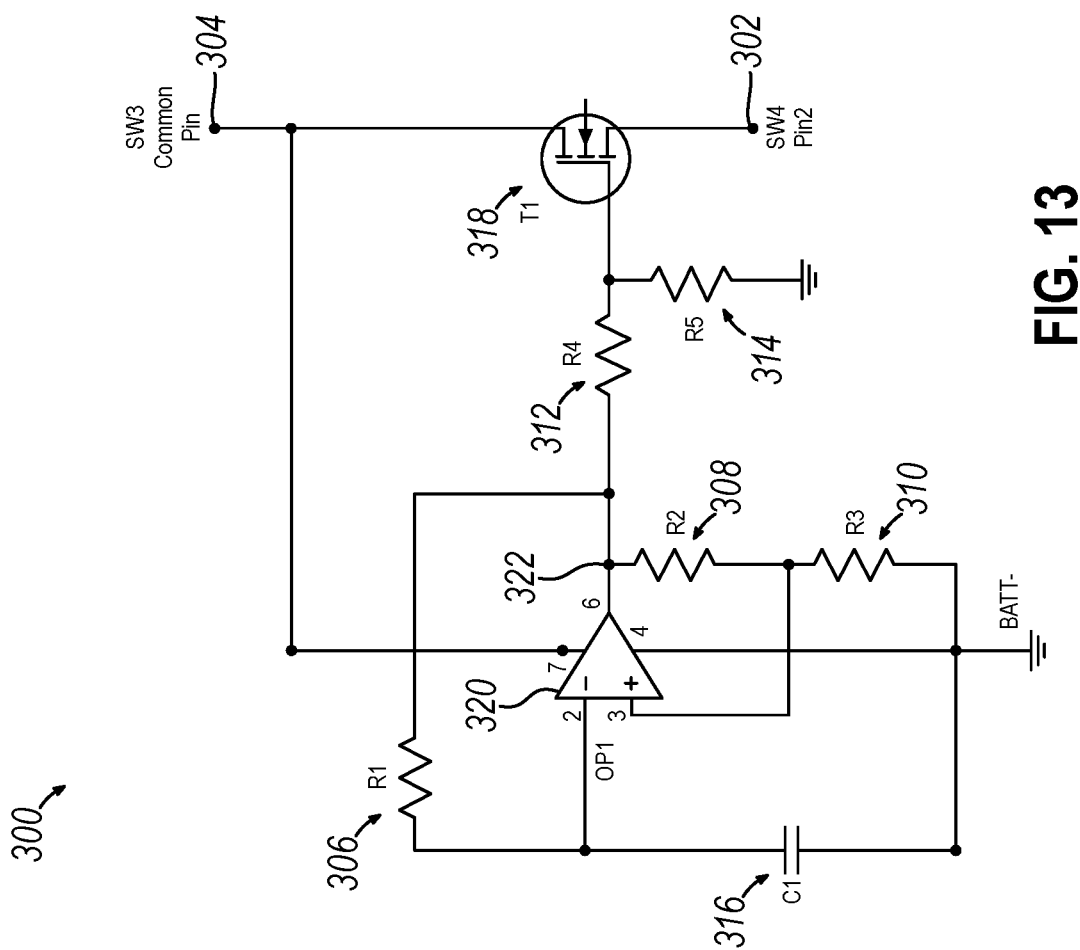
FIG. 13 depicts a third exemplary firing circuit that may be incorporated into the control circuit of FIG. 8.
Figure 14:
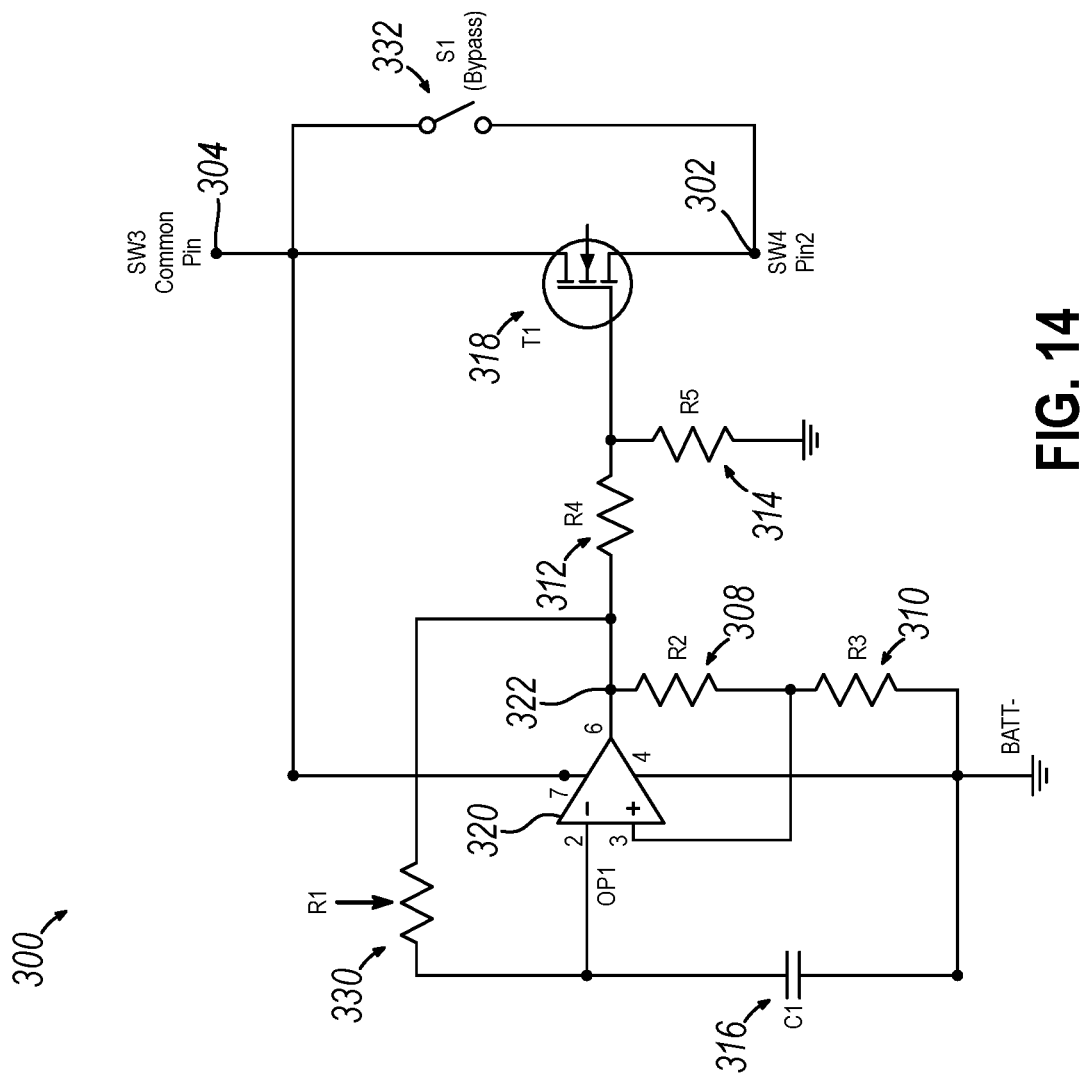
FIG. 14 depicts the firing circuit of FIG. 13, and including a pulse-adjustment mechanism and a pulse-bypass mechanism.

D. Exemplary Pulsating Firing Circuit Using an RC Circuit and Operational Amplifier FIGS. 13-14 depict another exemplary firing circuit (300) that may be incorporated into instrument (10). Particularly, node (302) of circuit (300) may be coupled with node (136) of control circuit (100), and node (304) of circuit (300) may be coupled with node (138) of control circuit (100) to include cutting edge (48) pulsing techniques to instrument (10). As shown, firing circuit (300) of this example includes several resistors (306, 308, 310, 312, 314), a capacitor (316), a transistor (318), and an operational amplifier (320). Transistor (220) can be a MOSFET transistor, for example, an SIS476DN-T1-GE3 N-Channel 30 V (D-S) MOSFET manufactured by Vishay Intertechnology, Inc. Alternatively, any other suitable kind of transistor may be used. Further, operational amplifier (320) can be, for example, an SG1536Y High Voltage Operational Amplifier manufactured by Microsemi Corporation. It will be appreciated that in other examples operational amplifier (320) may take various other suitable forms apparent to those skilled in the art in view of the teachings herein.

Operational amplifier (320) of the present example is configured to operate similar to a multi-vibrator to output an oscillating pulse signal or waveform. Particularly, output (322) of operational amplifier (320) oscillates between a HIGH state and a LOW state at a configurable frequency and pulse width. At the conclusion of the adjustable duration, operational amplifier (320) returns to a steady LOW state output. Thus, output (322) is configurable to resemble the waveform illustrated in FIG. 10.

Particularly, an RC circuit comprising resistors (306, 308, 310) and capacitor (316) is configurable by varying the resistor (306, 308, 310) and capacitor (316) values to adjust the oscillating square waveform provided at an output (322) of the operational amplifier (320). With reference to FIG. 10, the duration of one full period (192) can be calculated using the following approximate equation: $T=2*C*R1*\log e (1+R3/R2)$, wherein T is equal to the length of time of one period (192), C is capacitor (316), R1 is resistor (306), R2 is resistor (308) and R3 is resistor (310). In the present example, resistors (306, 308, 310) can be chosen at 0.2 megaohms, 27 kiloohms, and 27 kiloohms, respectively, and capacitor (316) can be chosen at 0.47 microfarads. Alternatively, any other suitable kinds of resistance and capacitance values may be used.

As firing circuit (300) is configured and operable to output a square wave voltage signal consisting of alternating HIGH and LOW voltage outputs at output node (322), transistor (318) can further be provided to selectively allow electrical current to pass between nodes (302, 304) as the output square waveform remains in the HIGH state at node (322), and disallow electrical current to pass between nodes (302, 304) as the multi-vibrator (i.e., the operation amplifier along with the RC circuit) output square waveform remains in the LOW state at node (322). In various examples, the duty cycle of signal (190) may be selected to be 0%, 25%, 50%, 75%, 100%; however, it should be understood that various alternative duty cycles may be configured.

In the present example, firing circuit (300) is not utilized to provide power to motor (140) to retract the cutting edge (48) from the tissue. Rather, once the cutting operating is complete, motor direction switch (108) of control circuit (100) toggles from the first state to the second state, causing the power signal to be removed from node (304), such that the output provided at node (322) of firing circuit (300) returns to a LOW state (194).

It may be desirable to provide a version of firing circuit (300) that includes features that allow a user of instrument (10) to adjust the pulsing motion (i.e., adjust the period (192)), or to selectively bypass the pulsing features altogether. FIG. 14 shows an example of firing circuit (300) that provides a user with the real-time ability to adjust the values of resistor (306) described above. Particularly, resistor (306) may be substituted with a potentiometer (330). Potentiometer (330) may be actuatable via one or more user-adjustable dials which may be included on instrument (10), such as on handle portion (20) of instrument (10). In one example, potentiometer (330) may be adjustable from 1-30 kiloohms and potentiometer (232) may be adjustable from 2 kiloohms-20 megaohms. However, it should be understood that the values of potentiometer (330) may be varied in order to meet the requirements of alternative configurations of instrument (10).

Also as depicted in FIG. 14, circuit (300) of the present example can include a bypass mechanism to permit an operator of instrument (10) to bypass the pulse-inducing features of firing circuit (300) and instead advance the cutting edge (48) of firing beam (14) in one continuous motion (i.e., via signal (190) having a duty cycle of 100%), such as shown in FIG. 8. In this example, a user-actuatable bypass switch (332), for example an ON/OFF rocker switch or other switch form commonly used in the art that is easily actuated by a user, may be included on an exterior surface of instrument (10), such as on handle portion (20) of instrument (10).

E. Exemplary Pulsating Firing Circuit Using a Relay

Figure 15:
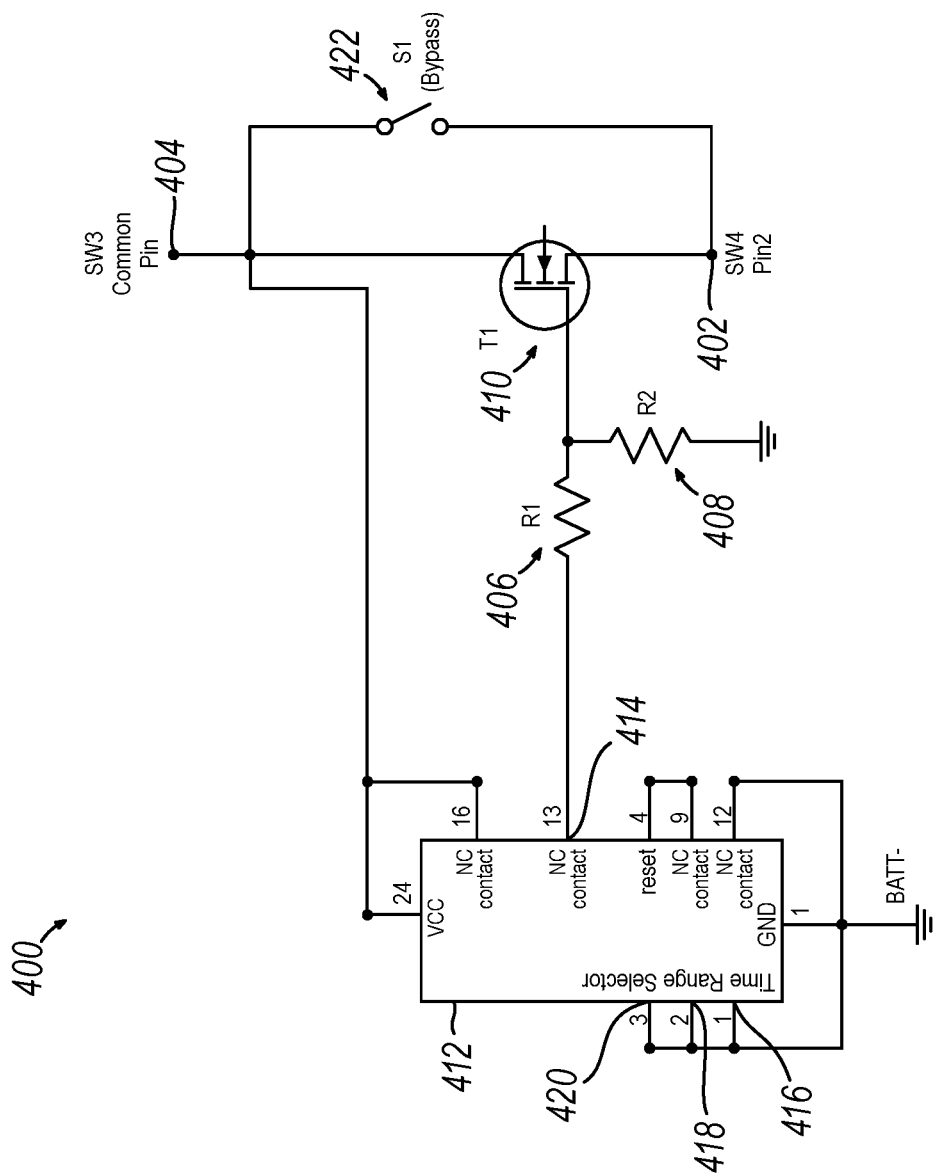
FIG. 15 depicts a fourth exemplary firing circuit that may be incorporated into the control circuit of FIG. 8.

FIG. 15 depicts another exemplary firing circuit (400) that may be incorporated into instrument (10). Particularly, node (402) of circuit (400) may be coupled with node (136) of control circuit (100), and node (404) of circuit (400) may be coupled with node (138) of control circuit (100) to include cutting edge (48) pulsing techniques to instrument (10). As shown, firing circuit (400) of this example includes resistors (406, 408), a transistor (410), and a relay (320). Transistor (410) can be a MOSFET transistor, for example, an SIS476DN-T1-GE3 N-Channel 30 V (D-S) MOSFET manufactured by Vishay Intertechnology, Inc. Alternatively, any other suitable kind of transistor may be used. Further, relay (412) can be, for example, an H3FA Solid State Timer manufactured by OMRON Corp. Alternatively, any other suitable kind of relay may be used. It will be appreciated that in other examples relay (412) may take various other suitable forms apparent to those skilled in the art in view of the teachings herein.

Relay (412) of the present example is configured to operate similar to a multi-vibrator to output an oscillating pulse signal or waveform. Particularly, output (414) of relay (412) oscillates between a HIGH state and a LOW state at a configurable frequency and pulse width. At the conclusion of the adjustable duration, relay (412) returns to a steady LOW state output unless and until the external trigger activates relay (412) again. Thus, output (414) is configurable to resemble the waveform illustrated in FIG. 10.

Particularly, relay (412) includes one or more inputs or time range selectors (416, 418, 420) that are user-adjustable to vary the oscillating square waveform provided at an output (414) of relay (412). In the present example, resistors (406, 408) can be chosen at 470 ohms, 10 kiloohms, respectively.

As firing circuit (400) is configured and operable to output a square wave voltage signal consisting of alternating HIGH and LOW voltage outputs at output node (414), transistor (410) can further be provided to selectively allow electrical current to pass between nodes (402, 404) as the output square waveform remains in the HIGH state at node (414), and disallow electrical current to pass between nodes (402, 404) as the multi-vibrator (i.e., the operation amplifier along with the RC circuit) output square waveform remains in the LOW state at node (414). In various examples, the duty cycle of signal (190) may be selected to be 0%, 25%, 50%, 75%, 100%; however, it should be understood that various alternative duty cycles may be configured.

In the present example, firing circuit (400) is not utilized to provide power to motor (140) to retract the cutting edge (48) from the tissue. Rather, once the cutting operating is complete, motor direction switch (108) of control circuit (100) toggles from the first state to the second state, causing the power signal to be removed from node (204), such that the output provided at node (414) of firing circuit (400) returns to a LOW state (194).

It may be desirable to provide a version of firing circuit (400) that includes features to bypass the pulse-inducing features of firing circuit (400) and instead advance the cutting edge (48) of firing beam (14) in one continuous motion (i.e., via signal (190) having a duty cycle of 100%), such as shown in FIG. 8. To that end, firing circuit (400) can include a user-actuatable bypass switch (422). Bypass switch (422) may be in the physical form of an ON/OFF rocker switch, or other switch form commonly used in the art that is easily actuated by a user, that is included on an exterior surface of instrument (10), such as on handle portion (20) of instrument (10).

F. Exemplary Pulsating Firing Circuit Using a Microcontroller

Figure 16:
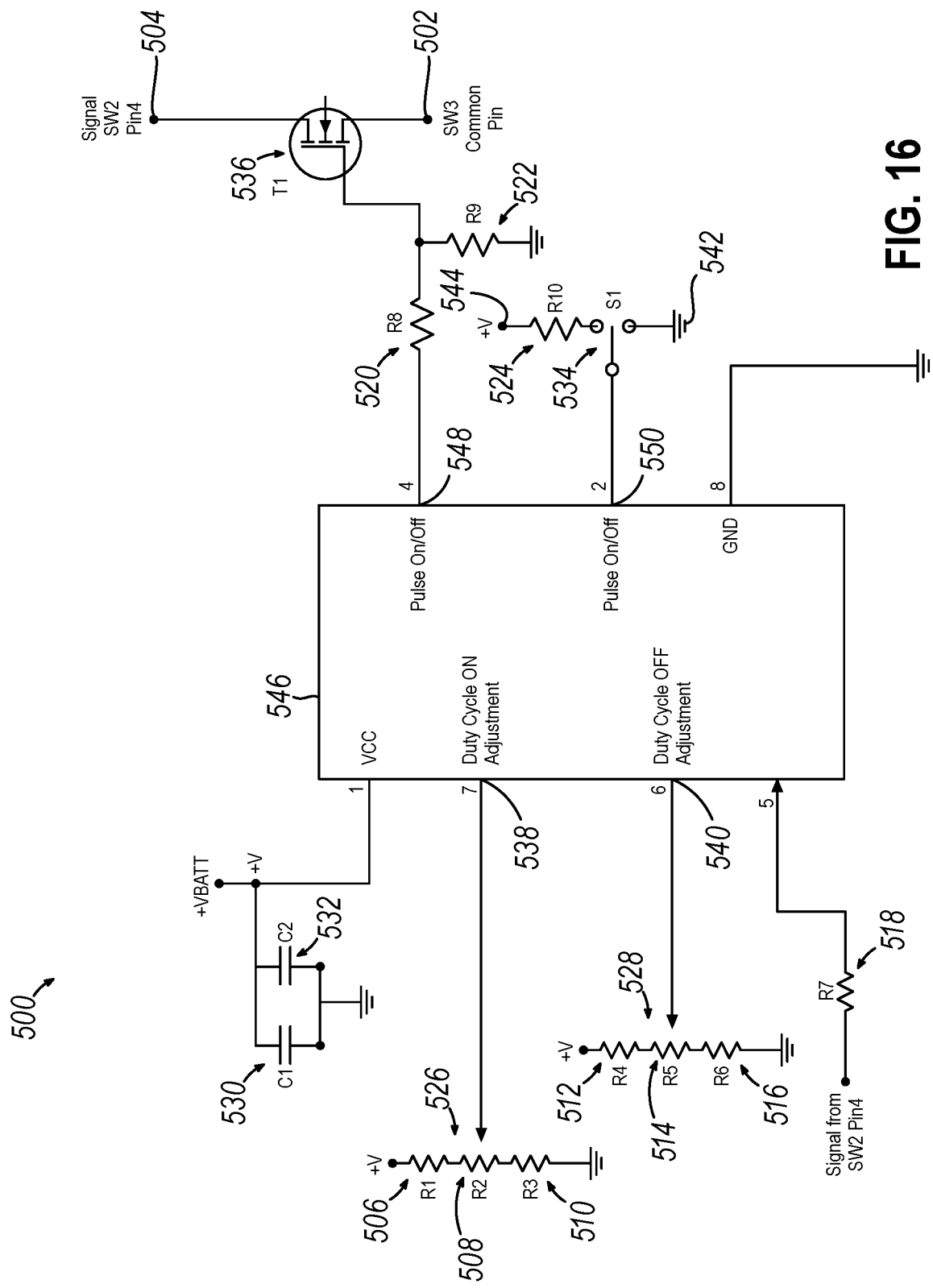
FIG. 16 depicts a fifth exemplary firing circuit that may be incorporated into the control circuit of FIG. 8.

FIG. 16 depicts another exemplary firing circuit (500) that may be incorporated into instrument (10). Particularly, node (502) of circuit (500) may be coupled with node (136) of control circuit (100), and node (504) of circuit (500) may be coupled with node (138) of control circuit (100) to include cutting edge (48) techniques to instrument (10). As shown, firing circuit (500) of this example includes resistors (506, 510, 512, 516, 518, 520, 522, 524), potentiometers (508, 514), capacitors (530, 532), a switch (534), a transistor (536), and a microcontroller (546). Transistor (536) can be a MOSFET transistor, for example, an SIS476DN-T1-GE3 N-Channel 30 V (D-S) MOSFET manufactured by Vishay Intertechnology, Inc. Alternatively, any other suitable kind of transistor may be used. Further, microcontroller (546) can be, for example, a PIC12F1501 8-Pin Flash, 8-Bit Microcontroller manufactured by Microchip Technology, Inc. It will be appreciated that in other examples microcontroller (546) may take various other suitable forms apparent to those skilled in the art in view of the teachings herein.

Microcontroller (546) of the present example is configured to operate similar to a multi-vibrator to output an oscillating pulse signal or waveform. Particularly, the signal at output node (548) of microcontroller (546) oscillates between a HIGH state and a LOW state at a configurable frequency and pulse width. At the conclusion of the adjustable duration, microcontroller (546) returns to a steady LOW state output unless and until the external trigger activates relay (412) again. The signal at output node (548) of microcontroller (546) is thus configurable to resemble the waveform illustrated in FIG. 10. In various examples, the duty cycle of signal (190) may be selected to be 0%, 25%, 50%, 75%, 100%; however, it should be understood that various alternative duty cycles may be configured.

Particularly, microcontroller (546) includes one or more inputs, ON duty cycle adjuster (538) and OFF duty cycle adjuster (540), that are user-adjustable to vary the oscillating square waveform provided in the signal at output node (548) of microcontroller (546). More specifically, resistors (506, 510) in combination with potentiometer (508) form a variable voltage divider operable to vary the input voltage to ON duty cycle adjuster (538) to adjust the duration of the HIGH states of the signal at output node (548). Further, resistors (512, 516) in combination with potentiometer (514) form a variable voltage divider operable to vary the input voltage to OFF duty cycle adjuster (540) to adjust the duration of the LOW states of the signal at output node (548). Potentiometers (508, 514) may be in the physical form of a user-adjustable dial, or other variable mechanism commonly used in the art that is easily actuated by a user, that is included on an exterior surface of instrument (10), such as on handle portion (20) of instrument (10). In the present example, resistors (506, 510, 512, 516, 518, 520, 522, 524), can be chosen at 1 kiloohms, 1 kiloohms, 1 kiloohms, 1 kiloohms, 470 ohms, 470 ohms, 10 kilohms, and 10 kilohms, respectively. Capacitors (530, 532) can be chosen to be 0.1 microfarads and 1.0 microfarads, respectively. However, it should be understood that all electrical component values may be varied in order to meet the requirements of alternative configurations of instrument (10).

As firing circuit (500) is configured and operable to output a square wave voltage signal consisting of alternating HIGH and LOW voltage outputs at output node (548), transistor (536) can further be provided to selectively allow electrical current to pass between nodes (502, 504) as the output square waveform remains in the HIGH state at output node (548), and disallow electrical current to pass between nodes (502, 504) as the multi-vibrator (i.e., the operation amplifier along with the RC circuit) output square waveform remains in the LOW state at output node (548).

In the present example, firing circuit (500) is not utilized to provide power to motor (140) to retract the cutting edge (48) from the tissue. Rather, once the cutting operating is complete, motor direction switch (108) of control circuit (100) toggles from the first state to the second state, causing the power signal to be removed from node (502), such that the output signal provided at output node (548) of firing circuit (500) returns to a LOW state (194).

It may be desirable to provide a version of firing circuit (500) that includes features to bypass the pulse-inducing features of firing circuit (500) and instead advance the cutting edge (48) in one continuous motion (i.e., via signal (190) having a duty cycle of 100%), such as shown in FIG. 8. To that end, firing circuit (500) can include a user-actuatable bypass switch (534) coupled with microcontroller (546) at output node (550) and configured to selectively disable pulsing features. For example, when bypass switch (534) is coupled with ground (542), microcontroller (546) can be configured to bypass the pulsing features and instead provide a signal at output node (548) a steady "one-shot" or monostable electrical pulse to motor (140) upon actuation of closure trigger (26). Alternatively, when bypass switch (534) is coupled with a battery or power supply voltage (544) through resistor (524), microcontroller (546) can be configured to enable the pulsing features and provide a signal at output node (548) an oscillating or astable electrical pulse to motor (140) upon actuation of closure trigger (26). Bypass switch (534) may be in the physical form of an ON/OFF rocker switch, or other switch form commonly used in the art that is easily actuated by a user, that is included on an exterior surface of instrument (10), such as on handle portion (20) of instrument (10).

It should be understood that the various additions and alternatives to control circuit (100) described above may be readily used with instrument (10). It should also be understood that, in some instances, the configuration and arrangement of the electrical components of control circuit (100) and firing circuits (150, 200, 300, 400, 500) may need to be varied in order to complement the configuration and arrangement of the features of instrument (10) described herein. Various suitable ways in which the alternatives to control circuit (100) and firing circuits (150, 200, 300, 400, 500) described herein may be incorporated into instrument (10) will be apparent to those skilled in the art in view of the teachings herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a body including a firing actuator; (b) a shaft extending distally from the body; (c) a motor configured to couple with a power source, wherein the motor is configured to activate in response to a firing actuation of the firing actuator; (d) an end effector disposed at a distal end of the shaft, wherein the end effector is operable to staple and sever tissue, wherein the end effector includes a cutting edge configured to selectively translate longitudinally between a proximal position and a distal position, wherein the cutting edge is configured to transition from the proximal position to the distal position to cut tissue in response to an activation of the motor; and (e) a control circuit operatively coupled with the motor and the firing actuator, wherein the control circuit is configured to generate a forward motor control signal to activate the motor in response to the firing actuation, wherein the forward motor control signal is configured to pulsate the cutting edge from the proximal position to the distal position to cut the tissue, wherein the pulsating forward motor control signal includes: (i) a first time duration including movement of the cutting edge distally from the proximal position to a second longitudinal position, (ii) a second time duration including ceased movement of the cutting edge, wherein the second time duration follows the first time duration, and (iii) a third time duration including movement of the cutting edge distally from the second longitudinal position toward the distal position, wherein the third time duration follows the second time duration.

Example 2

The surgical instrument of Example 1, wherein the control circuit is configured to determine that the cutting edge has reached the distal position, wherein the control circuit is further configured to generate a reverse motor control signal to activate the motor to transition the cutting edge from the distal position back to the proximal position.

Example 3

The surgical instrument of Examples 1 or 2, the control circuit further including a switch operable to reverse an electrical polarity provided to the motor by the power source, wherein the control circuit is configured to operate the switch in response to determining that the cutting edge has reached the distal position.

Example 4

The surgical instrument of any one or more of Examples 1 through 3, the control circuit further comprised of analog electrical components, wherein the analog electrical components are configured to oscillate the forward motor control signal between a high voltage signal and a low voltage signal, wherein the high voltage signal is operable to activate the motor, wherein the low voltage signal is operable to deactivate the motor.

Example 5

The surgical instrument of Example 4, the analog electrical components further comprising an RC circuit coupled with two transistors, wherein the RC circuit includes at least one resistor and at least one capacitor, wherein the RC circuit and two transistors are configured to oscillate the forward motor control signal.

Example 6

The surgical instrument of Example 4, the analog electrical components further comprising an integrated-circuit timing device.

Example 7

The surgical instrument of Example 4, the analog electrical components further comprising an operational amplifier configured to oscillate the forward motor control signal.

Example 8

The surgical instrument of Example 4, the analog electrical components further comprising a variable timer relay configured to oscillate the forward motor control signal.

Example 9

The surgical instrument of any one or more of Examples 1 through 8, the body further including a closing actuator, the end effector further including a stapling assembly configured to selectively move between an open position and a closed position in response to an actuation of the closing actuator, wherein the stapling assembly is configured to drive a plurality of staples from the stapling assembly into the tissue in response to an activation of the motor.

Example 10

The surgical instrument of any one or more of Examples 1 through 9, the control circuit further including a microcontroller, wherein the microcontroller is configured to oscillate the forward motor control signal between a high voltage signal and a low voltage signal, wherein the high voltage signal is operable to activate the motor, wherein the low voltage signal is operable to deactivate the motor.

Example 11

The surgical instrument of any one or more of Examples 1 through 10, wherein the forward motor control signal is configured with a duty cycle of less than 100% to pulsate the cutting edge from the proximal position to the distal position to cut tissue, the control circuit further including a bypass switch, wherein the bypass switch is selectively actuatable to increase the duty cycle to 100%.

Example 12

The surgical instrument of Example 11, wherein the bypass switch is positioned on an exterior surface of the body.

Example 13

The surgical instrument of any one or more of Examples 1 through 12, wherein the forward motor control signal is configured with a duty cycle of less than 100% to pulsate the cutting edge from the proximal position to the distal position to cut tissue, the control circuit further including an adjustable input feature, wherein the adjustable input feature is selectively operable to adjust the duty cycle.

Example 14

The surgical instrument of Example 13, wherein the adjustable input feature is positioned on an exterior surface of the body.

Example 15

The surgical instrument of any one or more of Examples 1 through 14, wherein the forward motor control signal is configured with a duty cycle of 50% to pulsate the cutting edge from the proximal position to the distal position to cut tissue.

Example 16

The surgical instrument of any one or more of Examples 1 through 15, wherein the forward motor control signal includes a frequency ranging from approximately 0.5 hertz to approximately 3 hertz.

Example 17

A surgical instrument, comprising: (a) a body including a firing actuator; (b) a motor configured to activate in response to a firing actuation of the firing actuator; (c) an end effector disposed at a distal end of the shaft, wherein the end effector is operable to staple and sever tissue, wherein the end effector includes a cutting edge configured to selectively translate longitudinally between a proximal position and a distal position, wherein the cutting edge is configured to transition from the proximal position to the distal position to cut tissue in response to an activation of the motor; and (d) a control circuit operatively coupled with the motor and the firing actuator, wherein the control circuit is configured to generate an oscillating motor control signal to activate the motor and pulsatingly transition the cutting edge from the proximal position to the distal position, wherein the control circuit is configured to thereafter generate a static motor control signal to activate the motor to transition the cutting edge from the distal position to the proximal position, wherein the pulsating transition includes (i) a first period including movement of the cutting edge distally from the proximal position to a second longitudinal position, (ii) a second period including ceased movement of the cutting edge, and (iii) a third period including movement of the cutting edge distally from the second longitudinal position toward the distal position.

Example 18

The surgical instrument of Example 17, the control circuit further comprised of analog electrical components configured to oscillate the oscillating motor control signal between a high voltage signal and a low voltage signal, wherein the high voltage signal is operable to activate the motor, wherein the low voltage signal is operable to deactivate the motor.

Example 19

A method of operating a surgical instrument, wherein the surgical instrument includes a body having a firing actuator, a shaft extending distally from the body, an end effector with a cutting edge disposed at a distal end of the shaft, a motor configured to couple with a power source, and a control circuit operatively coupled with the motor and the firing actuator, the method comprising: (a) in response to actuation of the firing actuator, transmitting a firing signal to the control circuit, wherein the control circuit is configured to generate a pulsating forward motor control signal to selectively activate the motor; (b) activating the motor upon receiving a first portion of the forward motor control signal from the control circuit, wherein activation of the motor translates the cutting edge distally; (c) maintaining the motor in the activated state for a first predetermined time period, wherein the cutting edge translates from a first longitudinal position to a second longitudinal position during the first predetermined time period, wherein the cutting edge translates through a first length of tissue during translation from the first longitudinal position to the second longitudinal position; (d) deactivating the motor upon receiving a second portion of the forward motor control signal from the control circuit to thereby cease distal translation of the cutting edge; (e) maintaining the motor in the deactivated state for a second predetermined time period, wherein the cutting edge remains in the second longitudinal position during the second predetermined time period, the end effector remaining adjacent to the tissue during the deactivated state; (f) activating the motor upon receiving a third portion of the forward motor control signal from the control circuit; (g) maintaining the motor in the activated state for a third predetermined time period, wherein the cutting edge translates from the second longitudinal position to a third longitudinal position during the third predetermined time period, wherein the cutting edge translates through a second length of tissue during translation from the second longitudinal position to the third longitudinal position; and (h) driving staples into the tissue during transit of the cutting edge from the first longitudinal position to the third longitudinal position.

Example 20

The method of Example 19, further comprising: (a) after the expiration of the third predetermined time period, reversing a power supply polarity of the motor provided by the power source; (b) generating a static reverse motor control signal to selectively activate the motor; (c) transmitting the reverse motor control signal to the motor; and (d) activating the motor upon receiving the static reverse motor control signal, wherein activation of the motor in response to receiving the reverse motor control signal translates the cutting edge proximally away from the cut tissue.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
(a) a body including a firing actuator;
(b) a shaft extending distally from the body;
(c) a motor configured to couple with a power source, wherein the motor is configured to activate in response to a firing actuation of the firing actuator;
(d) an end effector operatively coupled with the shaft, wherein the end effector is operable to staple and sever tissue, wherein the end effector includes a cutting edge configured to selectively translate longitudinally between a proximal position and a distal position, wherein the cutting edge is configured to transition from the proximal position to the distal position to cut tissue in response to an activation of the motor; and
(e) a control circuit operatively coupled with the motor and the firing actuator, wherein the control circuit is configured to generate a forward motor control signal that facilitates activation of the motor in response to the firing actuation, wherein the forward motor control signal is configured to pulsate the cutting edge from the proximal position to the distal position to cut the tissue, wherein the forward motor control signal includes:
(i) a first output level that facilitates movement of the cutting edge from the proximal position towards the distal position for a first time duration,
(ii) a second output level that facilitates stopping of the cutting edge at an intermediate position for a second time duration following the first time duration, wherein the intermediate position is between the proximal position and the distal position, and
(iii) a third output level that facilitates movement of the cutting edge from the intermediate position toward the distal position for a third time duration following the second time duration, and
wherein the control circuit receives or generates initial instructions for selecting the first time duration, the second time duration, the third time duration, and the intermediate position, wherein the receipt or generation of the initial instructions occurs entirely onboard the surgical instrument, and wherein the first output level, the second output level and the third output level cooperate to define a duty cycle of the forward motor control signal, the control circuit further including an adjustable input feature that is selectively operable to adjust the duty cycle.

2. The surgical instrument of claim 1, wherein the control circuit is configured to determine that the cutting edge has reached the distal position, wherein the control circuit is further configured to generate a reverse motor control signal to activate the motor, in response to determining that the cutting edge has reached the distal position, to transition the cutting edge from the distal position back to the proximal position.

3. The surgical instrument of claim 2, the control circuit further including a switch operable to reverse an electrical polarity provided to the motor by the power source, wherein the control circuit is configured to operate the switch in response to determining that the cutting edge has reached the distal position.

4. The surgical instrument of claim 1, wherein the control circuit further comprised of a plurality of analog electrical components, wherein the plurality of analog electrical components are configured to oscillate the forward motor control signal between a high voltage signal and a low voltage signal, wherein the high voltage signal is operable to activate the motor and defines the first output level and the third output level, and wherein the low voltage signal is operable to deactivate the motor and defines the second output level.

5. The surgical instrument of claim 4, the analog electrical components further comprising an RC circuit coupled with two transistors, wherein the RC circuit includes at least one resistor and at least one capacitor, and wherein the RC circuit and two transistors are configured to oscillate the forward motor control signal between the first output level, the second output level and the third output level.

6. The surgical instrument of claim 4, the analog electrical components further comprising an integrated-circuit timing device.

7. The surgical instrument of claim 4, the analog electrical components further comprising an operational amplifier configured to oscillate the forward motor control signal between the first output level, the second output level and the third output level.

8. The surgical instrument of claim 4, the analog electrical components further comprising a variable timer relay configured to oscillate the forward motor control signal between the first output level, the second output level and the third output level.

9. The surgical instrument of claim 1, the body further including a closing actuator, the end effector further including a stapling assembly configured to selectively move between an open position and a closed position in response to an actuation of the closing actuator, wherein the stapling assembly is configured to drive a plurality of staples from the stapling assembly into the tissue in response to an activation of the motor.

10. The surgical instrument of claim 1, the control circuit further including a microcontroller, wherein the microcontroller is configured to oscillate the forward motor control signal between a high voltage signal and a low voltage signal, wherein the high voltage signal is operable to activate the motor and defines the first output level and the third output level, and wherein the low voltage signal is operable to deactivate the motor and defines the second output level.

11. The surgical instrument of claim 1, wherein the adjustable input feature comprises a bypass switch that is selectively actuatable to set the duty cycle at 100%.

12. The surgical instrument of claim 11, wherein the bypass switch comprises a user-actuatable bypass switch.

13. The surgical instrument of claim 1, wherein the adjustable input feature comprises a user-actuatable input feature.

14. The surgical instrument of claim 13, wherein the first output level, the second output level and the third output level cooperate to define a duty cycle of the forward motor control signal that is 50%.

15. The surgical instrument of claim 1, wherein the forward motor control signal includes a frequency ranging from approximately 0.5 hertz to approximately 3 hertz.

16. A surgical instrument, comprising:
(a) a body including a firing actuator;
(b) a motor configured to activate in response to a firing actuation of the firing actuator;
(c) an end effector operatively coupled with a shaft, wherein the end effector is operable to staple and sever tissue, wherein the end effector includes a cutting edge configured to selectively translate longitudinally between a proximal position and a distal position, wherein the cutting edge is configured to transition from the proximal position to the distal position to cut tissue in response to an activation of the motor; and
(d) a control circuit operatively coupled with the motor and the firing actuator, wherein the control circuit is configured to generate an oscillating motor control signal that oscillates between:
(i) an active state that facilitates activation of the motor and thus translation of the cutting edge from the proximal position to the distal position, and between the proximal position and the distal position; and
(ii) an inactive state that facilitates deactivation of the motor and thus selective interruption of the translation of the cutting edge from the proximal position to the distal position such that the cutting edge periodically stops at different intermediate positions between the proximal position and the distal position, wherein the control circuit receives or generates initial instructions for selecting the different intermediate positions, wherein the receipt or generation of the initial instructions occurs entirely onboard the surgical instrument, and wherein the active state and the inactive state cooperate to define a duty cycle of the oscillating motor control signal, the control circuit further including an adjustable input feature that is selectively operable to adjust the duty cycle.

17. The surgical instrument of claim 16, the control circuit further comprised of analog electrical components configured to oscillate the oscillating motor control signal between a high voltage signal and a low voltage signal, wherein the high voltage signal is operable to activate the motor, and wherein the low voltage signal is operable to deactivate the motor.

18. The surgical instrument of claim 16, wherein the adjustable input feature comprises a bypass switch that is selectively actuatable to set the duty cycle at 100%.

19. A method of operating a surgical instrument, wherein the surgical instrument includes a body having a firing actuator, a shaft extending distally from the body, an end effector with a cutting edge operatively coupled with the shaft, a motor configured to couple with a power source, and a control circuit operatively coupled with the motor and the firing actuator, the method comprising:

(a) in response to actuation of the firing actuator, transmitting a firing signal to the control circuit, wherein the control circuit is configured to generate a pulsating forward motor control signal to selectively activate the motor;
(b) activating the motor upon receiving a first portion of the forward motor control signal from the control circuit, wherein activation of the motor translates the cutting edge from the proximal position towards the distal position;
(c) maintaining the motor in the activated state for a first predetermined time period to translate the cutting edge to an intermediate position located between the proximal position and the distal position, wherein the cutting edge translates through a first length of tissue during translation from the proximal position to the intermediate position;
(d) deactivating the motor upon receiving a second portion of the forward motor control signal from the control circuit to stop the cutting edge at the intermediate position;
(e) maintaining the motor in the deactivated state for a second predetermined time period to maintain the cutting edge in the intermediate position, the end effector remaining adjacent to the tissue during the deactivated state;
(f) activating the motor upon receiving a third portion of the forward motor control signal from the control circuit to initialize movement of the cutting edge;
(g) maintaining the motor in the activated state for a third predetermined time period to translate the cutting edge from the intermediate position towards the distal position during the third predetermined time period, wherein the cutting edge translates through a second length of tissue during translation from the intermediate position to the distal position; and
(h) driving staples into the tissue during translation of the cutting edge from the proximal position to the distal position, wherein the control circuit receives or generates initial instructions for selecting the first time duration, the second time duration, the third time duration, and the intermediate position, wherein the receipt or generation of the initial instructions occurs entirely onboard the surgical instrument, and wherein the first portion, the second portion, and the third portion cooperate to define a duty cycle of the forward motor control signal, the control circuit further including an adjustable input feature that is selectively operable to adjust the duty cycle.

20. The method of claim 19, further comprising:
(a) after the expiration of the third predetermined time period, reversing a power supply polarity of the motor provided by the power source;
(b) generating a reverse motor control signal to selectively activate the motor;
(c) transmitting the reverse motor control signal to the motor; and
(d) activating the motor upon receiving the static reverse motor control signal, wherein activation of the motor in response to receiving the reverse motor control signal translates the cutting edge proximally away from the cut tissue.

* * * * *